(12) United States Patent
Thompson et al.

(10) Patent No.: US 9,000,263 B2
(45) Date of Patent: Apr. 7, 2015

(54) INOSITOL POLYPHOSPHATE 2-KINASE GENES AND USES THEREOF

(75) Inventors: Mark Allen Thompson, Zionsville, IN (US); Holly Jean Butler, Indianapolis, IN (US); Yuejin Sun, Westfield, IN (US); Vipula Kiran Shukla, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1221 days.

(21) Appl. No.: 12/896,958

(22) Filed: Oct. 4, 2010

(65) Prior Publication Data

US 2011/0119786 A1    May 19, 2011

Related U.S. Application Data

(62) Division of application No. 11/662,530, filed as application No. PCT/US2005/032109 on Sep. 9, 2005.

(60) Provisional application No. 60/608,244, filed on Sep. 9, 2004.

(51) Int. Cl.
| | | |
|---|---|---|
| *C12N 15/82* | (2006.01) | |
| *C12N 15/63* | (2006.01) | |
| *C12N 15/09* | (2006.01) | |
| *A01H 5/00* | (2006.01) | |
| *C12N 9/12* | (2006.01) | |

(52) U.S. Cl.
CPC .......... *C12N 15/8243* (2013.01); *C12N 9/1205* (2013.01); *C12N 15/8245* (2013.01)

(58) Field of Classification Search
None
See application file for complete search history.

(56) References Cited

U.S. PATENT DOCUMENTS

| | | | |
|---|---|---|---|
| 5,689,054 | A | 11/1997 | Raboy |
| 6,111,168 | A | 8/2000 | Raboy |
| 6,197,561 | B1 | 3/2001 | Martino-Catt |
| 6,291,224 | B1 | 9/2001 | Martino-Catt |
| 2002/0102681 | A1 | 8/2002 | Martino-Catt |
| 2002/0102682 | A1 | 8/2002 | Martino-Catt |
| 2002/0110884 | A1 | 8/2002 | Martino-Catt |
| 2003/0009011 | A1 | 1/2003 | Shi |
| 2003/0079247 | A1 | 4/2003 | Shi |
| 2004/0214272 | A1* | 10/2004 | La Rosa et al. ............. 435/69.1 |

FOREIGN PATENT DOCUMENTS

| | | |
|---|---|---|
| WO | WO 99/05298 | 2/1999 |
| WO | WO 99/55882 | 11/1999 |
| WO | WO 00/73473 | 12/2000 |
| WO | WO 0192523 | 12/2001 |
| WO | WO 03000905 | 1/2003 |
| WO | WO 03/027243 | 4/2003 |

OTHER PUBLICATIONS

Verbsky et al. (2002)The Synthesis of Inositol Hexakisphosphate. J. Biol. Chem. 277:31857-31862.
Ives et al. (2000) Biochemical and Functional Characterization of Inositol 1,3,4,5,6-Pentakisphosphate 2-kinases, J. Biol. Chem 275: 36575-36583.
Phillippy et al. (1994) Purification and some Proper;ties of Inositol 1,3,4,5,6-Pentakisphosphate 2-kinases from Immature Soybean Seeds. J. Biol. Chenm. 269: 28393-28399.
Stevenson-Paulik et al. (2002) Moleculare and Biochemical Characteization of Two Plant Inositol Polyphosphate 6-/3-/5-Kinases. J. Biol. Chem. 277: 42711-42718.
York et al. (1999) A Phospholipase C-Dependent inositol Polyphosphate Kinase Pathway Required for Efficient Messenger RNA Export, Science 285:96-100.
Raboy, V. (2003) Myo-Inositol-1,2,3,4,5,6-Hexakisphosphate, Phytochemistry 64: 1033-1043.
Li, Xin. (2001) A Fast Neutron Deletion Mutagenesis-based Reverse Genetics System for Plants, The Plant Journal 27(3), 235-242.

* cited by examiner

*Primary Examiner* — Brent T Page
(74) *Attorney, Agent, or Firm* — Eric J. Kraus; Barnes & Thornburg LLP

(57) ABSTRACT

This invention relates to newly identified polynucleotides and polypeptides in the phytic acid biosynthetic pathways, variants and derivatives of the same; methods for making the polynucleotides, polypeptides, variants, derivatives and antagonists. In particular, the invention relates to polynucleotides encoding inositol polyphosphate 2-kinase (IPP2-K) and polypeptides exhibiting such activity to modulate the phytic acid biosynthesis in such a way as to decrease phytic acid and/or increase the non-phytic acid phosphorous, especially in corn or soy animal feedstuffs.

10 Claims, 7 Drawing Sheets

FIG. 1A

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| gi23559665 (1) | 100 | 78 | 85 | 50 | 44 | 44 | 43 | 44 | 41 | 18 | 19 | 30 | 76 | 76 | 78 |
| gi23559680 (2) |  | 100 | 80 | 49 | 42 | 43 | 42 | 43 | 39 | 17 | 18 | 28 | 70 | 70 | 100 |
| gi23559667 (3) |  |  | 100 | 50 | 44 | 44 | 44 | 46 | 42 | 19 | 20 | 31 | 82 | 82 | 80 |
| gi23559691 (4) |  |  |  | 100 | 42 | 44 | 43 | 44 | 40 | 22 | 22 | 31 | 41 | 41 | 49 |
| WO2003027243-1 (5) |  |  |  |  | 100 | 76 | 77 | 61 | 56 | 28 | 28 | 31 | 36 | 36 | 42 |
| WO2003027243-2 (6) |  |  |  |  |  | 100 | 98 | 60 | 53 | 27 | 28 | 31 | 35 | 35 | 43 |
| WO2003027243-3 (7) |  |  |  |  |  |  | 100 | 60 | 53 | 27 | 28 | 31 | 35 | 35 | 42 |
| WO2003027243-4 (8) |  |  |  |  |  |  |  | 100 | 65 | 27 | 27 | 32 | 39 | 39 | 43 |
| WO2003027243-5 (9) |  |  |  |  |  |  |  |  | 100 | 22 | 22 | 28 | 39 | 39 | 39 |
| WO2003027243-6 (10) |  |  |  |  |  |  |  |  |  | 100 | 95 | 8 | 11 | 12 | 17 |
| WO2003027243-7 (11) |  |  |  |  |  |  |  |  |  |  | 100 | 9 | 12 | 12 | 18 |
| zmIPP2-K (12) |  |  |  |  |  |  |  |  |  |  |  | 100 | 27 | 27 | 29 |
| gi23559669 (13) |  |  |  |  |  |  |  |  |  |  |  |  | 100 | 99 | 70 |
| gi23559671 (14) |  |  |  |  |  |  |  |  |  |  |  |  |  | 100 | 70 |
| gi23559685 (15) |  |  |  |  |  |  |  |  |  |  |  |  |  |  | 100 |

Multiple Alignment Algorithm

FIG. 2

Comparison of predicted amino acid sequence from putative plant IPP2-K genes.

IPP2-K Genomic Structure
9681 bp

In vitro activity of IPP2-K enzyme on IP4 and IP5 substrates.

Lane 1: IPP2-K plus inositol 1,4,5,6 tetra*kis*phosphate substrate
Lane 2: IPP2-K plus inositol 1,3,4,5,6 penta*kis*phosphate substrate
Lane 3: IPP2-K plus inositol 1,4,5,6 tetra*kis*phosphate substrate
Lane 4: IPP2-K plus inositol 1,3,4,5,6 penta*kis*phosphate substrate

INOSITOL POLYPHOSPHATE 2-KINASE GENES AND USES THEREOF

This application claims the benefit of U.S. Provisional Application No. 60/608,244, filed on Sep. 9, 2004; PCT Application No. US05/032,109 filed Sep. 9, 2005; and, U.S. Utility application Ser. No. 11/662,530 filed Mar. 9, 2007.

The present invention relates to the field of plant molecular biology. Specifically, the present invention relates to the identification and use of genes encoding the enzyme inositol polyphosphate 2-kinase (IPP2-K), which is involved in the phytic acid biosynthesis pathway in plants and to the use of these genes and mutants thereof to reduce the levels of phytic acid, and/or to increase the levels of non-phytic acid phosphorous in plant seed and food or feed containing such seed.

The role of phosphorous in animal nutrition is well recognized. Eighty percent of the phosphorous in the body of animals is found in the skeleton, providing structure to the animal. Twenty percent of the phosphorous in animals can be found in soft tissues, where it is involved in a myriad of biochemical reactions including the synthesis and activity of DNA, RNA, phospholipids and some B vitamins.

Though phosphorous is critical to animal health, not all phosphorous in feed is bio-available. Myo-inositol 1,2,3,4,5,6-hexa-kis-phosphate, commonly known as phytic acid, is an abundant molecule in many plant seeds and vegetative tissue such as roots and tubers. Phytic acid salts (or phytates) are the major storage form of phosphorous in seeds, typically representing from 65% to 80% of seed total phosphorous (P). When seed-based diets are consumed by non-ruminants, the consumed phytic acid forms salts of several nutritionally important minerals in the digestive tract. Excretion of these salts reduces the retention and utilization (i.e., the bioavailability) of both the phosphorous and the minerals. Consequently, this results in mineral deficiencies in both humans and animals fed the seed. Moreover, phytic acid bound phosphorous in animal waste contributes to surface and ground water pollution.

Several approaches have been proposed to reduce the negative impact that phytic acid content in seed has on diet, phosphorous and mineral retention, and the environment. Approaches include removing dietary phytic acid by post-harvest intervention and reducing seed phytic acid content genetically. Seed containing reduced phytic acid is claimed in U.S. Pat. No. 5,689,054 (maize) and U.S. Pat. No. 6,111,168 (soybean). Alteration of phytate levels through manipulation of myo-inositol 1-phosphate synthase is discussed in WO 00/73473, WO 99/05298, U.S. Pat. No. 6,197,561 and U.S. Pat. No. 6,291,224. Alteration of phytate levels through shunting into ononitol with inositol methyl transferase is discussed in WO 99/37786. U.S. Pat. No. 6,197,561 proposes changing phytate levels through alteration of a number of additional enzymes, including phosphatidylinositol-3-kinase, myo-inositol 1,3,4-triphosphate 5/6-kinase, myo-inositol monophosphatase-3, inositol polyphosphate 5-phosphatase, D-myo-inositol-3-phosphate synthase, D-myo-inositol triphosphate 3-kinase, myo-inositol transporter, maize phytase, phosphatidylinositol transfer protein, phosphatidyloinositol-4-phosphate-5-kinase, phosphatidylinositol-specific phospholipase, myo-inositol monophosphatase-1, phosphatidylinositol 4-kinase, phosphatidylinositol (4,5) bis-phosphate 5-phosphatase, phosphatidylinositol synthase. Plant/seed expression of phytase, an enzyme capable of degrading phytate, is also disclosed in U.S. Pat. No. 6,399,861, U.S. Pat. No. 6,303,766, U.S. Pat. No. 5,994,628, U.S. Pat. No. 5,714,474 and U.S. Pat. No. 5,543,576. US 2003/0009011 (WO 02/059324) discloses inositol polyphosphate kinase genes and use for modulating phytate levels, and additionally proposes consensus sequences to identify other inositol polyphosphate kinase genes. US 2003/0079247 (WO 03/027243) discloses additional inositol polyphosphate kinase genes described as the inositol 1,3,4-trisphosphate 5/6 kinase gene family. The lpa2 mutant described in U.S. Pat. No. 5,689,054 above contains a mutation in a member of this gene family (see also Plant Physiol. 2003 February; 131(2): 507-15).

Despite these approaches, a need still exists to improve the nutritional content of plants, particularly corn, by reducing the levels of phytic acid and increasing the levels of non-phytic acid phosphorous.

The IPP2-K enzyme catalyzes multiple steps leading to the formation of phytic acid. It catalyzes, for example: the reactions of ATP+inositol 1,4,5,6-tetrakisphosphate→ADP+inositol pentakisphosphate and ATP+inositol 1,3,4,5,6-pentakisphosphate→ADP+inositol 1,2,3,4,5,6-hexaphosphate. Additionally, this enzyme catalyzes the reactions of ATP+inositol 1,4,6-triphosphate→ADP+inositol 1,2,6-triphosphate. A reduction in the activity of the IPP2-K enzyme in developing plant seeds would interrupt phytic acid synthesis, thereby reducing the level of phytic acid in seeds and making phosphorous more metabolically available to animals that are fed the seed. The present invention addresses the need to improve phosphate bioavailability by providing nucleic acid sequences encoding all or a portion of the IPP2-K enzyme and the tools for the manipulation of the phytic acid biosynthetic pathway in plant cells.

According to the present invention, there is provided an isolated plant polynucleotide comprising a member selected from the group consisting of:
(a) a polynucleotide comprising SEQ ID NO: 1; (b) a polynucleotide comprising at least 65% sequence identity to SEQ ID NO: 1, wherein the % sequence identity is based on the entire coding region and is determined by GAP 10 analysis using default parameters; (c) a polynucleotide comprising at least 46% sequence identity to SEQ ID NO: 1, wherein the % sequence identity is based on the entire coding region and is determined by GAP 10 analysis using default parameters; (d) a polynucleotide encoding a polypeptide comprising SEQ ID NO: 2; (e) a polynucleotide comprising a sequence of a nucleic acid amplified from plant nucleic acid using primers based on SEQ ID NOS: 1 and 3 (f) a polynucleotide which selectively hybridizes, under stringent conditions to a polynucleotide of SEQ ID NO: 1, wherein the hybridization conditions include a wash step in 0.1×SSC at 60° C.; (g) a polynucleotide coding for a corn inositol polyphosphate 2-kinase; (h) a polynucleotide coding for a plant inositol polyphosphate 2-kinase; and (i) a polynucleotide complementary to a polynucleotide of (a) through (h).

The invention also relates to an isolated protein comprising a member selected from the group consisting of: (a) a polypeptide comprising at least 25 contiguous amino acids of SEQ ID NO: 2; (b) a polypeptide comprising at least 45% sequence identity compared to the full-length of SEQ ID NO: 2, wherein the percent sequence identity is based on the entire sequence length and is determined by GAP 10 analysis using default parameters; (c) a polypeptide encoded by a nucleic acid of claim 1; (d) a polypeptide encoded by a nucleic acid of SEQ ID NO: 1; and, (e) a polypeptide having the sequence set forth in SEQ ID NO: 2.

A further aspect of the present invention is an isolated plant polypeptide comprising an amino acid sequence which has at least 65% sequence identity to SEQ ID NO: 2, wherein the polypeptide has inositol polyphosphate 2-kinase activity.

Yet another aspect of the present invention is a method of disrupting inositol polyphosphate 2-kinase activity levels in a plant tissue, comprising: subjecting a plant tissue to mutagenesis; obtaining a DNA sample from the plant tissue subjected to mutagenesis or descendants thereof; and assaying the DNA sample for a lesion in a gene encoding inositol polyphosphate 2-kinase.

Furthermore, the present invention relates to a corn seed containing an artificially-induced lesion in a gene encoding inositol polyphosphate 2-kinase.

Additionally, the present invention relates to a canola (*Brassica napus*) seed containing an artificially-induced lesion in a gene encoding inositol polyphosphate 2-kinase.

In yet another embodiment, the present invention is directed to a method of decreasing the level of phytic acid in animal feed, comprising: producing animal feed from a plant containing a lesion in a gene encoding inositol polyphosphate 2-kinase, wherein the animal feed has a decreased level of available phytate.

The present invention also relates to a method of decreasing the level of phosphorous in animal waste comprising: providing animal feed from a plant including a lesion in a gene encoding inositol polyphosphate 2-kinase.

Moreover, the present invention embraces a non-lethal mutant seed of a cereal plant species characterized by low phytic acid content relative to parental germplasm of the species, wherein the mutant seed has altered inositol polyphosphate 2-kinase activity.

Additionally, the present invention relates to a purified antibody generated by using a polypeptide comprising SEQ ID NO: 2 as an immunogen.

Also, the present invention relates to a vector for transformation of plant cells comprising (a) antisense nucleotide sequences substantially complementary to (1) a corresponding portion of one strand of a DNA molecule encoding inositol polyphosphate 2-kinase, wherein the DNA molecule encoding inositol polyphosphate 2-kinase hybridizes under low stringency conditions with SEQ ID NO:1 or (2) a corresponding portion of an RNA sequence encoded by the DNA molecule encoding inositol polyphosphate 2-kinase; and (b) regulatory sequences operatively linked to the antisense nucleotide sequences such that the antisense nucleotide sequences are expressed in a plant cell into which it is transformed.

Mention should be made that the present invention further relates to an antisense oligonucleotide or polynucleotide encoding an RNA molecule which is substantially complementary to a corresponding portion of an RNA transcript of a plant inositol polyphosphate 2-kinase gene, wherein said plant gene hybridizes under low stringency conditions with SEQ ID NO:1

Yet another aspect of the present invention is a method of generating a mutant plant having a desired trait linked to a gene knockout, the method comprising: providing a collection plant seeds; treating said collection of plant seeds with either chemical mutagens, such as EMS, or irradiation selected from the group consisting of UV, gamma-irradiation, X-rays, and fast neutrons; and selecting the mutant plants having the desired trait.

One further aspect of the present invention is an isolated plant inositol polyphosphate 2-kinase protein comprising at least one of the motifs selected from the group consisting of:

DAXDWXYXXEGXXNLXLXYXGSSP,

VEIKXKCGFLXXSXXIXXXNXKXXXXRXXMXQXCKXXXXXISXXSEY

XPLDLFSGSKXXXXXAIKXXXXTPQNXXXXXXGSLXXGG,

ISXXSEYXPLDLFSGSK,

LXXLLXXQKLDXXIEGXIHXYY, and

LIXXTAXDCSXMISF.

FIG. 1A shows the similarity of maize IPP2-K claimed herein to other maize inositol kinases. Low level of sequence similarity suggests that maize IPP2-K is a novel inositol phosphate kinase.

FIG. 1B shows the phylogenetic relationship between maize IPP2-K protein sequences and inositol-phosphate kinases from maize and other species. Putative IPP2-K genes from diverse range of species (from human to *Arabidopsis*) are closely related. In contrast, other inositol phosphate kinases are grouped into different branch of the phylogenic tree. The alignment is created using the Clustal W algorithm (Nucleic Acid Research, 22 (22): 4673-4680, 1994). Briefly, a crude similarity between all pairs of sequences is calculated, called a "Parities alignment." These scores are then used to calculate a "guide tree" or dendrogram, which tells the multiple alignment stage the order in which to align the sequences for the final multiple alignment. Having calculated the dendrogram, the sequences are aligned in larger and larger groups until the entire sequences are incorporated in the final alignment.

FIG. 2 shows a comparison of predicted amino acid sequences from putative plant IPP2-K genes

Figure 5:
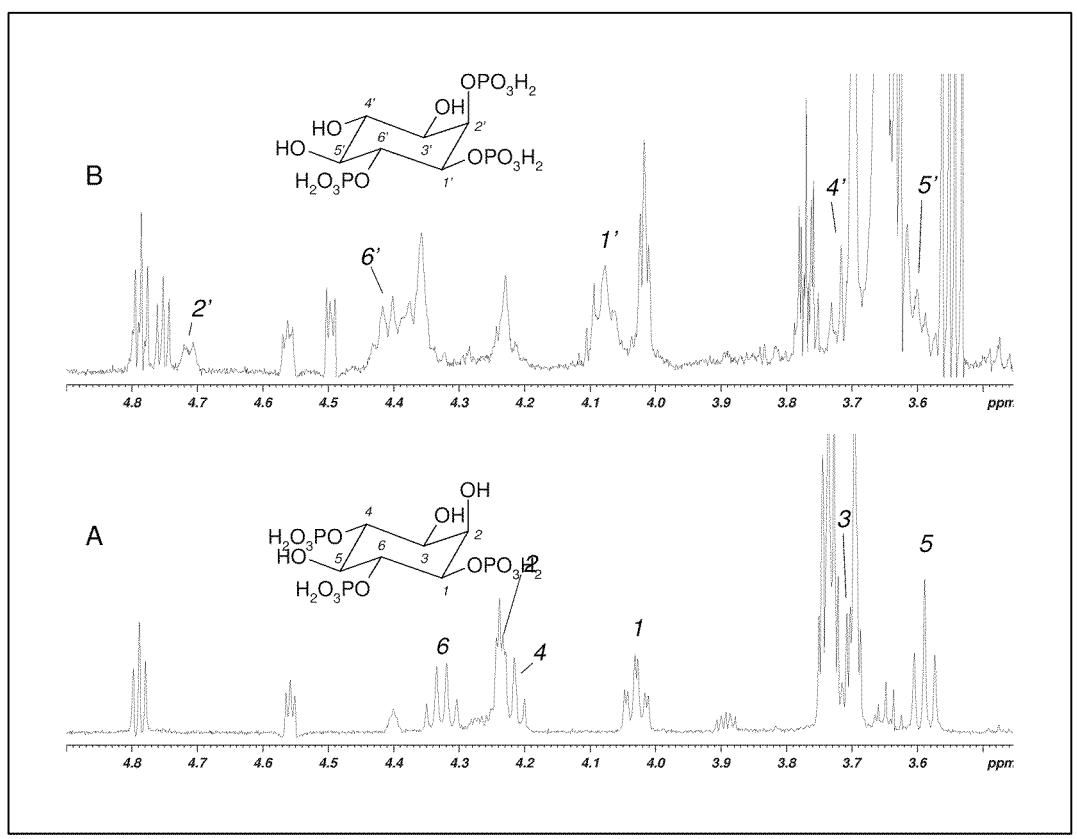

FIG. 5 shows the in vitro conversion of inositol 1,4,6-triphosphate into inositol 1,2,6-triphosphate in the presence of IPP2-K enzyme and ATP as detected by $^1$H-NMR. 600 MHz $^1$H NMR spectra of inositol-1,4,6-triphosphate solution in $D_2O$ containing ATP and DTT. (A) Immediately before the addition of IPP2-K enzyme. (B) two hours after addition of IPP2-K enzyme. Peaks corresponding to Inositol-1,4,6-triphosphate and inositol-1,2,6-triphosphate are indicated. Unlabeled peaks in the region 3.5-3.8 ppm correspond to DTT, while those 3.8-4.8 ppm arise from ATP and ADP. The 3' proton of Inositol-1,2,6-triphosphate lies underneath the DTT peaks at 3.67 ppm.

Figure 6:
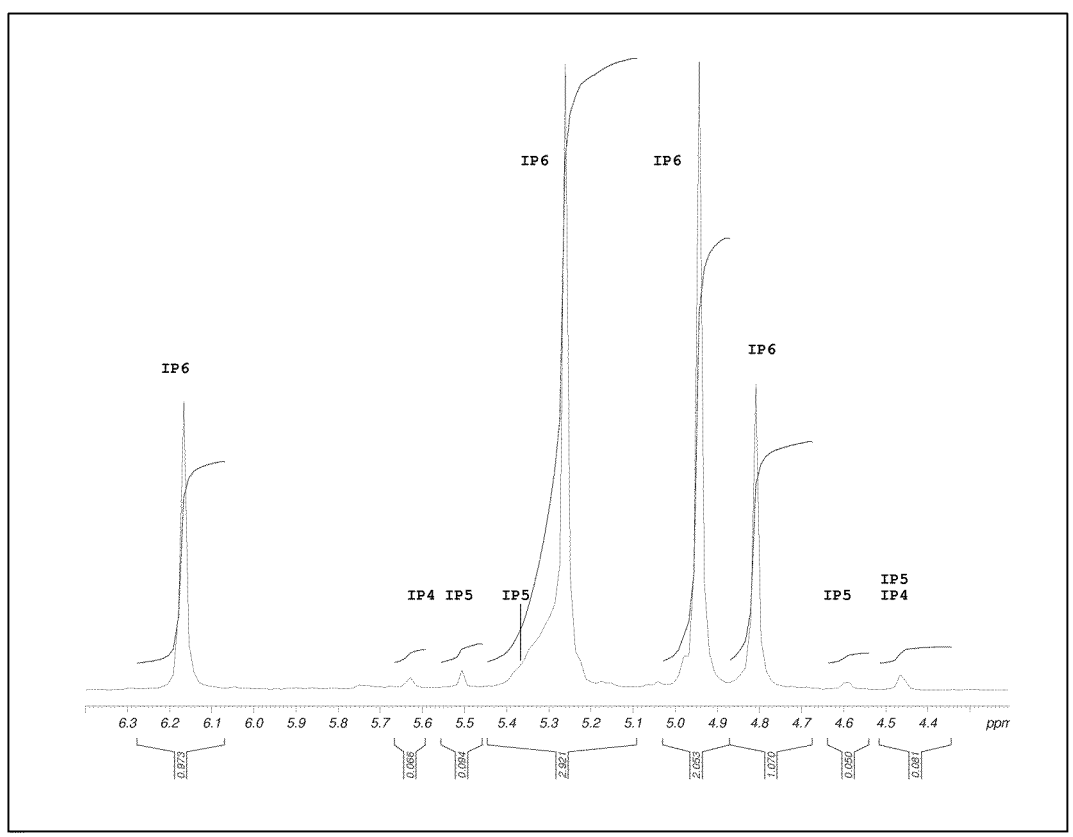

FIG. 6 shows the phosphorous-NMR spectra of seed extract from maize inbred line DAS5XH751, indicating the inositol phosphate species present. Phosphorous NMR spectra of seed extract from inbred maize line DAS 5XH751. Spectra were obtained at 400.13 MHz on a Bruker DRX-400 NMR spectrometer fitted with a 5-mm 1H/13C/19F/31P probe. Peaks are labeled to indicate the inositol phosphate species giving rise to that signal. IP6: phytate (inositol hexakisphosphate); IP5: inositol pentakisphosphate; IP4: inositol tetrakisphosphate.

SEQ ID NO:1 is the nucleotide sequence for the cDNA encoding a maize IPP2-K in inbred line DAS5XH751 seeds.

SEQ ID NO:2 is the deduced amino acid sequence of an IPP2-K derived from the nucleotide sequence of SEQ ID NO:1.

SEQ ID NO:3 is the nucleotide sequence for the genomic DNA encoding IPP2-K from maize inbred line 5XH751.

Definitions are herein provided to facilitate understanding of the invention. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

"Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, RNAi, or other RNA that may not be translated but yet has an effect on cellular processes.

The term "complementary DNA" (cDNA) refers to a single-stranded DNA molecule that can be formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule derived from a mRNA molecule.

The term "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

The term "expression" refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

DNA-binding proteins which use zinc finger (ZF) recognition motifs may be designed to recognize and modify specific DNA sequences or change expression. Such engineered zinc fingers (ZFs) can be used to directly alter a gene in its native environment when they are operatively linked to a nuclease (ZFNs). Site-preferential, or site-specific nuclease cleavage, mediated through the ZF binding, can effect changes in expression or activity. Changes in target genes may include replacements with designed DNA via homologous recombination, and gene disruptions from insertions or deletions. Examples of ZFN-mediated genome changes are found in Biol. Chem. 1999 July-August; 380(7-8):841-848; Molecular and Cellular Biology 21(1): 289-297, 2001; Genetics 161: 1169-1175, 2002. By contrast, ZFs may indirectly modulate expression and activity when designed to function as transcription factors which interact with the gene in trans. Such ZFPs may be engineered either to enhance or reduce transcription (refs). Regulation of ZFP expression may be constitutive, tissue-specific, temporally-specific, or inducible. Examples of ZFP-mediated changes in expression are found in Proc. Nat. Acad. Sci. 99(20): 13290-13295, 2002; Proc. Nat. Acad. Sci. 99(20): 13296-13301, 2002; Plant Cell Physiol. 43(12): 1465-1472, 2002; review in Curr. Opin. Plant Biol. 6: 163-168, 2003.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. An additional copy or copies of an endogenous gene may be re-introduced into the host organism in a different chromosomal location, leading to contextual and expression level differences. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genomic DNA" refers to chromosomal DNA and can include introns. An intron is an intervening sequence. It is a non-coding sequence of DNA within a gene that is transcribed into heterogenous nuclear RNA (hnRNA) but is then removed by RNA splicing in the nucleus, leaving a mature mRNA which is then translated in the cytoplasm. The regions at the ends of an intron are typically self-complementary, allowing a hairpin structure to form naturally in the hnRNA.

The term "inositol polyphosphate 2-kinase polynucleotide" or "IPP2-K polynucleotide" refers to a polynucleotide encoding a polypeptide with at least inositol polyphosphate 2-kinase activities, or a polynucleotide capable of modulating the expression of IPP2-K mRNA or protein in a host cell. The term also includes fragments, variants, homologs, alleles or precursors (e.g., preproteins or proproteins) with any one of the above-stated activities.

The term "IPP2-K" refers to inositol polyphosphate 2-kinase with regard to any nucleic acid or polypeptide, or the associated functional activity. The IPP2-K enzymes of the present invention have a broad substrate specificity and can phosphorylate several inositol phosphate species including but not limited to inositol triphosphate, inositol tetrakisphosphate and inositol pentakisphosphate using adenosine triphosphate (ATP) as the phosphate donor, resulting in the products adenosine diphosphate (ADP) and a phosphorylated inositol phosphate.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

The term "lesion" refers to any molecular alteration of a nucleic acid relative to wild type plant nucleic acids. For instance, a lesion can be a deletion, inversion, insertion, duplication, transversion, transition or a rearrangement in a nucleic acid sequence.

The term "motif" refers to short regions of conserved sequences of nucleic acids or amino acids that comprise part of a longer sequence.

The term "non-ruminant animal" means an animal with a simple stomach divided into the esophageal, cardia, fundus and pylorus regions. A non-ruminant animal additionally implies a species of animal without a functional rumen. A rumen is a section of the digestive system where feedstuff/food is soaked and subjected to digestion by microorganisms before passing on through the digestive tract. This phenomenon does not occur in a non-ruminant animal. The term non-ruminant animal includes but is not limited to humans, swine, poultry, cats and dogs.

The term "phytic acid" refers to myo-inositol tetraphosphoric acid, myo-inositol pentaphosphoric acid, myo-inositol hexaphosphoric acid and their derivatives such as: 5-pyrophosphate-inositol (1,3,4,6) tetrakisphosphate, 5-pyrophosphate-inositol (1,2,3,4,6)pentakisphosphate and 5,6-bis-pyrophosphate-inositol (1,2,3,4) tetrakisphosphate. As a salt with cations, phytic acid is "phytate."

The term "plant" includes plants and plant parts including but not limited to plant cells and plant tissues such as leaves, stems, roots, flowers, pollen, and seeds. The class of plants that can be used in the present invention is generally as broad as the class of higher and lower plants amenable to mutagenesis including angiosperms (monocotyledonous and dicotyledonous plants), gymnosperms, ferns and multicellular algae.

The term "polynucleotide" refers to any nucleic acid and includes single or multi-stranded polymers of deoxyribonucleotide or ribonucleotide bases. Nucleic acids may also include fragments and modified nucleotides. Therefore, as used herein, the terms "nucleic acid" and "polynucleotide" are used interchangeably.

The term "promoter" typically refers to a DNA sequence which directs the transcription of a structural gene to produce RNA. Typically, a promoter is located in the region 500 base pairs upstream of a gene, proximal to the transcription start site. If a promoter is an inducible promoter, then the rate of transcription increases or decreases in response to an exogenous or endogenous inducing agent. In contrast, the rate of transcription is regulated to a lesser degree by an inducing agent if the promoter is a constitutive promoter.

The terms "transcription regulatory region" and "regulatory region" refer to the section of DNA which regulates gene transcription. A regulatory region may include a variety of cis-acting elements, including, but not limited to, promoters, enhancers and hormone response elements. Also, since introns and 5' UTR have been known to influence transcription, a transcription regulatory region can include such sequences.

The term "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using programs from the GCG package (Genetics Computer Group, Madison, Wis.). Multiple alignment of the sequences was performed using the Clustal method of alignment (Higgins, D. G. and Sharp, P. M. (1989) CABIOS. 5:151-153) with the default parameters (GAP PENALTY=10, GAP LENGTH PENALTY=10) (hereafter, Clustal algorithm). Default parameters for pairwise alignments using the Clustal method were KTUPLE 1, GAP PENALTY=3, WINDOW=5 and DIAGONALS SAVED=5.

A "substantial portion" of an amino acid or nucleotide sequence refers to enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403-410; see also www.ncbi.nlm.nih.gov/BLAST/). In general, a sequence of ten or more contiguous amino acids or thirty or more nucleotides is necessary to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "variant" refers to substantially similar sequences. Generally, nucleic acid sequence variants of the invention will have at least 46%, 48%, 50%, 52%, 53%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98% or 99% sequence identity to the native nucleotide sequence, wherein the % sequence identity is based on the entire sequence and is determined by GAP 10 analysis using default parameters. Generally, polypeptide sequence variants of the invention will have at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the native protein, wherein the % sequence identity is based on the entire sequence and is determined by GAP 10 analysis using default parameters. GAP uses the algorithm of Needleman and Wunsch (J. Mol. Biol. 48:443-453, 1970) to find the alignment of two complete sequences that maximizes the number of matches and minimizes the number of gaps.

The term "variant" also refers to substantially similar sequences that contain amino acid sequences highly similar to the motifs contained within the invention and optionally required for the biological function of the invention. Generally, polypeptide sequence variants of the invention will have at least 85%, 90% or 95% sequence identity to the conserved amino acid residues in the defined motifs.

Standard recombinant DNA and molecular cloning techniques used herein are well known in the art and are described more fully in Sambrook, J. & Russell, D. W., Molecular Cloning: A Laboratory Manual; Cold Spring Harbor Laboratory Press. Cold Spring Harbor, N.Y. 2001 (hereinafter "Sambrook").

Variants included in the invention may contain individual substitutions, deletions or additions to the nucleic acid or polypeptide sequences which alter, add or delete a single amino acid or a small percentage of amino acids in the encoded sequence. A "conservatively modified variant" is an alteration which results in the substitution of an amino acid with a chemically similar amino acid. When the nucleic acid is prepared or altered synthetically, advantage can be taken of known codon preferences of the intended host.

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other inositol triphosphate kinases, inositol tetrakisphosphate kinases, inositol pentakisphosphate kinases, or inositol polyphosphate 2-kinases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primer DNA labeling, nick translation, or end-labeling techniques, or RNA probes using available in vitro transcription systems.

In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) PNAS USA 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Invitrogen, Carlsbad Calif.), specific 3' or 5' cDNA fragments can be isolated (Ohara et al., (1989) PNAS USA 86:5673; Loh et al., (1989) Science 243:217). Products generated by the 3' and 5' RACE procedures can be combined to generate full-length cDNAs (Frohman, M. A. and Martin, G. R., (1989) Techniques 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) Adv. Immunol. 36:1; Sambrook).

The nucleic acid fragments of the instant invention may be used to create transgenic plants in which the disclosed inositol polyphosphate 2-kinase enzyme is present at lower levels than normal.

Reducing or eliminating expression of genes encoding inositol polyphosphate 2-kinase in plants for some applications is desirable. To accomplish this, a chimeric gene designed for co-suppression of the instant phytic acid biosynthetic enzyme can be constructed by linking a gene or gene fragment encoding an inositol polyphosphate 2-kinase to plant promoter sequences. Alternatively, a chimeric gene designed to express antisense RNA for all or part of the instant nucleic acid fragment can be constructed by operatively linking the gene or gene fragment in reverse orientation to plant promoter sequences. Either the co-suppression or antisense chimeric genes could be introduced into plants via transformation wherein expression of the corresponding endogenous genes are reduced or eliminated.

An alternative methodology to achieve gene knockdown involves the use of RNA interference (RNAi) and post-transcriptional gene silencing (PTGS) [Fraser et al. (2000), Nature, 408, 325-330; Gonczy et al. (2000), Nature, 408(331-336)]. Introduction of double-stranded RNA (dsRNA) into the cells of these organisms leads to the sequence-specific degradation of homologous gene transcripts. The long double-stranded RNA molecules are reduced to small 21-23 nucleotide interfering RNAs (siRNAs) by the action of an endogenous ribonuclease, Dicer. (Bernstein et al. (2001), Nature, 409, 363-366; Grishok et al. (2000), Science, 287 (5462), 2494-7; Zamore et al. (2000), Cell, 101(1), 25-33; Knight, S. W. and B. L. Bass. (2001), Science, 293(5538), 2269-2271).

The instant inositol polyphosphate 2-kinase (or portions thereof) may be produced in heterologous host cells, particularly in the cells of microbial hosts, and can be used to prepare antibodies to the these proteins by methods well known to those skilled in the art. The antibodies are useful for detecting inositol polyphosphate 2-kinase in situ in cells or in vitro in cell extracts. Preferred heterologous host cells for production of the instant inositol polyphosphate 2-kinase are microbial hosts. Microbial expression systems and expression vectors containing regulatory sequences that direct high level expression of foreign proteins are well known to those skilled in the art. Any of these could be used to construct a chimeric gene for production of the instant inositol polyphosphate 2-kinase. This chimeric gene could then be introduced into appropriate microorganisms via transformation to provide high level expression of the encoded phytic acid biosynthetic enzyme.

The isolated nucleic acids of the present invention can be made using (a) standard recombinant methods, (b) synthetic techniques, or combinations thereof. In some embodiments, the polynucleotides of the present invention can be cloned, amplified, or otherwise constructed from a monocot or dicot. Typical examples of monocots are corn, sorghum, barley, wheat, millet, rice, or turf grass. Typical dicots include soybeans, safflower, sunflower, canola, alfalfa, potato, or cassava.

Functional fragments included in the invention can be obtained using primers which selectively hybridize under stringent conditions. Primers are generally at least 12 bases in length and can be as high as 200 bases, but will generally be from 15 to 75, or more likely from 15 to 50 bases. Functional fragments can be identified using a variety of techniques such as restriction analysis, Southern analysis, primer extension analysis, PCR and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Current Protocols in Molecular Biology, Brent et al., Eds., Wiley and Sons, New York (2003) (hereinafter known as Brent). Also, see generally, McPherson (ed.), DIRECTED MUTAGENESIS: A Practical Approach, (IRL Press, 1991). Thus, the present invention also encompasses DNA molecules comprising nucleotide sequences that have substantial sequence similarity with the inventive sequences.

With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the claimed invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 50 can be so altered. Thus, for example, 1, 2, 3, 14, 25, 37, 45 or 50 alterations can be made. Conservatively modified variants typically provide similar biological activity as the unmodified polypeptide sequence from which they are derived. For example, substrate specificity, enzyme activity, or ligand/receptor binding is generally at least 20%, 30%, 40%, 50%, 60%, 70%, 80%, or 90% of the native protein for its native substrate. Conservative substitution tables providing functionally similar amino acids are well known in the art.

For example, the following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V); and
6) Phenylalanine (F), Tyrosine (Y), Tryptophan (W).

See also, (Creighton (1984) Proteins W. H. Freeman and Company), other acceptable conservative substitution patterns known in the art may also be used, such as the scoring matrices of sequence comparison programs like the GCG package, BLAST, or CLUSTAL for example.

The claimed invention also includes "shufflents" produced by sequence shuffling of the inventive polynucleotides to obtain a desired characteristic. Sequence shuffling is described in PCT publication No. 96/19256. See also, Zhang, J. H., et al., Proc. Natl. Acad. Sci. USA 94:4504-4509 (1997).

The present invention also includes the use of 5' and/or 3' UTR regions for modulation of transcription or translation of heterologous coding sequences. Positive sequence motifs include translational initiation consensus sequences (Kozak, Nucleic Acids Res. 15:8125 (1987)) and the 7-methylguanosine cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. Cell. Biol. 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the GCG, the University of Wisconsin Genetics Computer Group (see Devereaux et al., Nucleic Acids Res. 12:387-395 (1984).

For example, the inventive nucleic acids or their antisense counterparts can be optimized for enhanced expression in plants of interest. See, for example, Perlak et al. (1991) Proc. Natl. Acad. Sci. USA 88:3324-3328; and Murray et al. (1989) Nucleic Acids Res. 17:477-498, the disclosure of which is incorporated herein by reference. In this manner, the polynucleotides can be synthesized utilizing plant-preferred codons.

The present invention provides subsequences comprising isolated nucleic acids containing at least 20 contiguous bases of the claimed sequences. For example the isolated nucleic acid includes those comprising at least 25, 30, 40, 50, 60, 70, 80, 90, 100, 200, 300, 400, 500, 600, 700, 800, 900, 1,000, 1,500 or 2,000 contiguous nucleotides of the claimed sequences. Subsequences of the isolated nucleic acid can be used to modulate or detect gene expression by introducing into the subsequences compounds which bind, intercalate, cleave and/or crosslink to nucleic acids.

The nucleic acids of the claimed invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence, or a GST fusion sequence, provides a convenient means to purify the proteins of the claimed invention.

A polynucleotide of the claimed invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 2004 (La Jolla, Calif.); and Amersham BioSciences, Inc, Catalog 2004 (Piscataway, N.J.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in Plant Molecular Biology: A Laboratory Manual, Clark, Ed., Springer-Verlag, Berlin (1997); and Brent. Total RNA and mRNA isolation kits are commercially available from vendors such as Stratagene (La Jolla, Calif.), Clonetech (Palo Alto, Calif.), Amersham Biosciences (Piscataway, N.J.), and 5'-3' (Paoli, Pa.). See also, U.S. Pat. Nos. 5,614, 391; and, 5,459,253.

Typical cDNA synthesis protocols are well known to the skilled artisan and are described in such standard references as: Plant Molecular Biology: A Laboratory Manual, Clark, Ed., Springer-Verlag, Berlin (1997); and Brent. cDNA synthesis kits are available from a variety of commercial vendors such as Stratagene or Pharmacia.

An exemplary method of constructing a greater than 95% pure full-length cDNA library is described by Carninci et al., Genomics 37:327-336 (1996). Other methods for producing full-length libraries are known in the art. See, e.g., Edery et al., Mol. Cell. Biol. 15(6):3363-3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, Nucl. Acids. Res. 18(19):5705-5711 (1990); Patanjali et al., Proc. Natl. Acad. U.S.A. 88:1943-1947 (1991); U.S. Pat. Nos. 5,482,685 and 5,637,685; and Soares et al., Proc. Natl. Acad. Sci. USA 91:9228-9232 (1994).

Subtracted cDNA libraries are another means to increase the proportion of less abundant CDNA species. See, Foote et al. in, Plant Molecular Biology: A Laboratory Manual, Clark, Ed., Springer-Verlag, Berlin (1997); Kho and Zarbl, Technique 3(2):58-63 (1991); Sive and St. John, Nucl. Acids Res. 16(22):10937 (1988); Brent; and, Swaroop et al., Nucl. Acids Res. 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, and Methods in Enzymology, Vol. 152: Guide to Molecular Cloning Techniques, Berger and Kimmel, Eds., San Diego: Academic Press, Inc. (1987), Brent; Plant Molecular Biology: A Laboratory Manual, Clark, Ed., Springer-Verlag, Berlin (1997). Kits for construction of genomic libraries are also commercially available.

The cDNA or genomic library can be screened either using PCR directly with methods known to those skilled in the art, or using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1.×SSC at 60° C. Typically the time of hybridization is from 4 to 16 hours.

An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Brent. Often, cDNA libraries will be normalized to increase the representation of relatively rare cDNAs.

The nucleic acids of the invention can be amplified from nucleic acid samples, such as plant nucleic acid samples, using amplification techniques. For instance, polymerase chain reaction (PCR) technology can be used to amplify the sequences of polynucleotides of the present invention and related polynucleotides directly from genomic DNA libraries, cDNA libraries, or a library generally constructed from nuclear transcripts at any stage of intron processing. Libraries can be made from a variety of plant tissues such as ears, seedlings, leaves, stalks, roots, pollen, or seeds. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Brent, as well as Mullis et al., U.S. Pat. No. 4,683,202 (1987); and, PCR Protocols A Guide to Methods and Applications, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. BioTechniques, 22(3):481-486 (1997).

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook, and Innis et al. (1990), PCR Protocols: A Guide to Methods and Applications (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetra. Lett. 22:1859-1862 (1981); the solid phase phosphoramidite triester method described by Beaucage and Caruthers, Tetra. Lett. 22(20): 1859-1862 (1981), e.g., using an automated synthesizer, e.g., as described in Needham-VanDevanter et al., Nucleic Acids Res. 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Sambrook) of restriction-digested plant genomic DNA may be probed with the nucleic acid fragments of the instant invention. The resulting banding patterns may then be subjected to genetic analyses using computer programs such as MapMaker (Lander et al., (1987) Genomics 1:174-181) to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) Am. J. Hum. Genet. 32:314-331).

The production and use of plant gene-derived probes for use in genetic mapping is described in R. Bernatzky, R. and Tanksley, S. D. (1986) Plant Mol. Biol. Reporter 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: Nonmammalian Genomic Analysis: A Practical Guide, Academic press 1996, pp. 319-346, and references cited therein).

In another embodiment, nucleic acid probes derived from the instant nucleic acid sequences may be used in direct fluorescence in situ hybridization (FISH) mapping (Trask, B. J. (1991) Trends Genet. 7:149-154). Although current methods of FISH mapping favor use of large clones (several to several hundred KB; see Laan, M. et al. (1995) Genome Research 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) J. Lab. Clin. Med. 114(2):95-96), polymorphism of PCR-amplified fragments (CAPS; Sheffield, V. C. et al. (1993) Genomics 16:325-332), allele-specific ligation (Landegren, U. et al. (1988) Science 241:1077-1080), nucleotide extension reactions (Sokolov, B. P. (1990) Nucleic Acid Res. 18:3671), Radiation Hybrid Mapping (Walter, M. A. et al. (1997) Nature Genetics 7:22-28) and Happy Mapping (Dear, P. H. and Cook, P. R. (1989) Nucleic Acid Res. 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in populations carrying mutations in all possible genes (Ballinger and Benzer, (1989) Proc. Natl. Acad. Sci. USA 86:9402; Koes et al., (1995) Proc. Natl. Acad. Sci. USA 92:8149; Bensen et al., (1995) Plant Cell 7:75). The latter approach may be accomplished in several ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the inositol polyphosphate 2-kinase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. Thirdly, mutations may be mapped within specific genes using single-strand endonucleases capable of cleaving at mismatches (Till et al. (2004) Nucleic Acids Res. 32:2632-41), a method known as TILLING. Finally, deletions may be identified using PCR methods known to those skilled in the art, as described in US Patent Application 20050053975 and as followed in the present examples. With each method, a plant containing a mutation in the endogenous gene encoding an inositol polyphosphate 2-kinase can be identified and obtained. This mutant plant can then be used to determine or confirm the natural function of the gene product.

Proteins of the present invention include proteins having the disclosed sequences as well proteins coded by the disclosed polynucleotides. In addition, proteins of the present invention include proteins derived from the native protein by deletion, addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) Proc. Natl. Acad. Sci. USA 82:488-492; Kunkel et al. (1987) Methods Enzymol. 154:367-382; Sambrook; U.S. Pat. No. 4,873,192; and the references cited therein; herein incorporated by reference. Guidance as to appropriate amino acid substitutions that do not affect biological activity of the protein of interest would be readily understood by those skilled in the art. Conservative substitutions, such as exchanging one amino acid with another having similar properties, may be preferred.

In constructing variants of the proteins of interest, modifications to the nucleotide sequences encoding the variants can generally be made such that variants continue to possess the desired activity. The isolated proteins of the present invention include a polypeptide comprising at least 25 contiguous amino acids encoded by any one of the nucleic acids of the present invention, or polypeptides that are conservatively modified variants thereof. The proteins of the present invention or variants thereof can comprise any number of contiguous amino acid residues from a polypeptide of the present invention, wherein that number is selected from the group of integers consisting of from 25 to the number of residues in a full-length polypeptide of the present invention. Optionally, this subsequence of contiguous amino acids is at least 25, 30, 40, 50, 60, 70, 80, 90, 100, 150, 200, 250, 300, 350, 400, 450, or 500 amino acids in length.

The present invention includes catalytically active polypeptides (i.e., enzymes). Catalytically active polypeptides will generally have a specific activity of at least about 20%, 30%, 40%, 50%, 60%, 70%, 80%, 90%, or 95% that of the native (non-synthetic), endogenous polypeptide. Further, the substrate specificity ($K_{cat}/K_m$) may be optionally substantially similar to the native (non-synthetic), endogenous polypeptide for each activity. Typically, the $K_m$ will be at least about 10%, 20%, 30%, 40%, 50%, 60%, 70%, 80%, 90%, or 95% that of the native (non-synthetic), endogenous polypeptide for any given substrate. Methods of assaying and quantifying measures of enzymatic activity and substrate specificity ($K_{cat}/K_m$), are well known to those of skill in the art. See, e.g., Segel, Biochemical Calculations, 2nd ed., John Wiley and Sons, New York (1976).

The present invention includes modifications that can be made to an inventive protein. In particular, it may be desirable to diminish the activity of the gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids or peptides (e.g., poly His, GST, etc) placed on either terminus to create conveniently located restriction sites or termination codons or purification A protein of the present invention, once expressed, can be isolated from cells by lysing the cells and applying standard protein isolation techniques to the lysates. The monitoring of the purification process can be accomplished by using Western blot techniques or radioimmunoassay or other standard immunoassay techniques. Expression cassettes are also available which direct the expressed protein to be secreted from the cell into the media. In these cases, the expressed protein can be purified from the cell growth media using standard protein purification techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in The Peptides: Analysis, Synthesis, Biology. Vol. 2: Special Methods in Peptide Synthesis, Part A.; Merrifield et al., J. Am. Chem. Soc. 85:2149-2156 (1963), and Stewart et al., Solid Phase Peptide Synthesis, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide) are known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, Protein Purification Principles and Practice, Springer-Verlag: New York (1982); Deutscher, Guide to Protein Purification, Academic Press (1990). For example, antibodies may be raised to the proteins as described herein. Purification from E. coli can be achieved following procedures described in U.S. Pat. No. 4,511,503.

Means of detecting the proteins of the present invention are not critical aspects of the present invention. The proteins can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: Antibodies in Cell Biology, Asai, Ed., Academic Press, Inc. New York (1993); Basic and Clinical Immunology 7th Edition, Stites & Ten, Eds. (1991). Moreover, the immunoassays of the present invention can be performed in any of several configurations, e.g., those reviewed in Enzyme Immunoassay, Maggio, Ed., CRC Press, Boca Raton, Fla. (1980); Tijan, Practice and Theory of Enzyme Immunoassays, Laboratory Techniques in Biochemistry and Molecular Biology, Elsevier Science Publishers B. V., Amsterdam (1985); Harlow and Lane, supra; Immunoassay: A Practical Guide, Chan, Ed., Academic Press, Orlando, Fla. (1987); Principles and Practice of Immunoassays, Price and Newman Eds., Stockton Press, NY (1991); and Non-isotopic Immunoassays, Ngo, Ed., Plenum Press, NY (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand molecule (e.g., streptavidin) which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 0,2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of catalytically active polypeptides of the present invention. The method comprises contacting a polypeptide of the present invention with a compound whose ability to bind to or modulate enzyme activity is to be determined. The polypeptide employed will have at least 20%, 30%, 40%, 50%, 60%, 70%, 80%, 90% or 95% of the specific activity of the native, full-length polypeptide of the present invention (e.g., enzyme). Methods of measuring enzyme kinetics are well known in the art. See, e.g., Segel, Biochemical Calculations, 2nd ed., John Wiley and Sons, New York (1976).

Antibodies can be raised to a protein of the present invention, including individual, allelic, strain, or species variants, and fragments thereof, both in their naturally occurring (full-length) forms and in recombinant or synthetic forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., Basic and Clinical Immunology, 4th ed., Stites et al., Eds., Lange Medical Publications, Los Altos, Calif., and references cited therein; Harlow and Lane, Supra; Goding, Monoclonal Antibodies: Principles and Practice, 2nd ed., Academic Press, New York, N.Y. (1986); and Kohler and Milstein, Nature 256:495-497 (1975).

Other suitable techniques involve selection of libraries of recombinant antibodies in phage or similar vectors (see, e.g., Huse et al., Science 246:1275-1281 (1989); and Ward et al., Nature 341:544-546 (1989); and Vaughan et al., Nature Biotechnology 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., Nature Biotech. 14:845-851 (1996). Also, recombinant immunoglobulins may be produced. See, Cabilly, U.S. Pat. No. 4,816,567; and Queen et al., Proc. Natl. Acad. Sci. U.S.A. 86:10029-10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention may be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

The present invention further provides a method for modulating (i.e., decreasing) the concentration or composition of the polypeptides of the claimed invention in a plant or part thereof. Modulation can be effected by increasing or decreasing the concentration and/or the composition (i.e., the ratio of the polypeptides of the claimed invention) in a plant.

The method comprises transforming a plant cell with an expression cassette comprising an antisense nucleotide sequences substantially complementary to (1) a corresponding portion of one strand of a DNA molecule encoding inositol polyphosphate 2-kinase, wherein the DNA molecule encoding inositol polyphosphate 2-kinase hybridizes under low stringency conditions with SEQ ID NO:1 or (2) a corresponding portion of an RNA sequence encoded by the DNA molecule encoding inositol polyphosphate 2-kinase; and (b) regulatory sequences operatively linked to the antisense nucleotide sequences such that the antisense nucleotide sequences are expressed in a plant cell into which it is transformed.

In some embodiments, the content and/or composition of polypeptides of the present invention in a plant may be decreased by altering, in vivo or in vitro, the promoter of a non-isolated gene of the present invention to down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to decrease the concentration and/or composition of polypeptides of the present invention in the plant. Plant forming conditions are well known in the art.

In general, content of the polypeptide is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In certain embodiments, the polypeptides of the present invention are modulated in monocots or dicots, for example maize, soybeans, sunflower, safflower, sorghum, canola, wheat, alfalfa, rice, barley and millet.

The method of transformation is not critical to the present invention; various methods of transformation are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein, can be used to construct an expression cassette which can be introduced into the desired plant. Isolated nucleic acid acids of the present invention can be introduced into plants according to techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., Ann. Rev. Genet. 22:421-477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in Plant Cell, Tissue and Organ Culture, Fundamental Methods, Eds. O. L. Gamborg and G C Phillips, Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., Embo J. 3:2717-2722 (1984). Electroporation techniques are described in Fromm et al., Proc. Natl. Acad. Sci. U.S.A. 82:5824 (1985). Ballistic transformation techniques are described in Klein et al., Nature 327:70-73 (1987).

*Agrobacterium tumefaciens*-meditated transformation techniques are well described in the scientific literature. See, for example Horsch et al., Science 233:496-498 (1984), and Fraley et al., Proc. Natl. Acad. Sci. 80:4803 (1983). For instance, *Agrobacterium* transformation of maize is described in U.S. Pat. No. 5,981,840. *Agrobacterium* transformation of soybean is described in U.S. Pat. No. 5,563,055.

Other methods of transformation include (1) *Agrobacterium rhizogenes*-mediated transformation (see, e.g., Lichtenstein and Fuller In: Genetic Engineering, Vol. 6, P. W. J. Rigby, Ed., London, Academic Press, 1987; and Lichtenstein, C. P. and Draper, J. In: DNA Cloning, Vol. 11, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., Plant Cell Physiol. 25:1353 (1984)), and (3) the vortexing method (see, e.g., Kindle, Proc. Natl. Acad. Sci. USA 87:1228 (1990)).

DNA can also be introduced into plants by direct DNA transfer into pollen as described by Zhou et al., Methods in Enzymology 101:433 (1983); D. Hess, Intern Rev. Cytol., 107:367 (1987); Luo et al., Plant Mol. Biol. Reporter 6:165 (1988). Expression of polypeptide coding polynucleotides can be obtained by injection of the DNA into reproductive organs of a plant as described by Pena et al., Nature 325:274 (1987). DNA can also be injected directly into the cells of immature embryos and the rehydration of desiccated embryos as described by Neuhaus et al., Theor. Appl. Genet. 75:30 (1987); and Benbrook et al., in Proceedings Bio Expo 1986, Butterworth, Stoneham, Mass., pp. 27-54 (1986).

Animal and lower eukaryotic (e.g., yeast) host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., Biochemical Methods in Cell Culture and Virology, Dowden, Hutchinson and Ross, Inc. (1977).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., The Plant Cell 2:603-618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., Protoplasts Isolation and Culture, Handbook of Plant Cell Culture, Macmillan Publishing Company, New York, pp. 124-176 (1983); and Binding, Regeneration of Plants, Plant Protoplasts, CRC Press, Boca Raton, pp. 21-73 (1985).

The regeneration of plants containing the foreign gene introduced by *Agrobacterium* can be achieved as described by Horsch et al., Science, 227:1229-1231 (1985) and Fraley et al., Proc. Natl. Acad. Sci. U.S.A. 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., Ann. Rev. Plant Phys. 38:467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, The Maize Handbook, Freeling and Walbot, Eds., Springer, New York (1994); Corn and Corn Improvement, 3rd edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Transgenic plants of the present invention can be homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated. Alternatively, propagation of heterozygous transgenic plants could be accomplished through apomixis.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Plant Molecular Biology: A Laboratory Manual, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G Landis Company, Austin, Tex., pp. 7-21.

The particular method of genotyping in the present invention may employ any number of molecular marker analytic techniques such as, but not limited to, amplification fragment length polymorphisms (AFLPs). AFLPs are the product of allelic differences between DNA PCR-amplification fragments caused by nucleotide sequence variability. Thus, the present invention further provides a means to follow segregation of a gene or nucleic acid of the present invention as well as chromosomal sequences genetically linked to these genes or nucleic acids using such techniques as AFLP analysis.

Plants which can be used in the method of the invention include monocotyledonous and dicotyledonous plants. Preferred plants include maize, wheat, rice, barley, oats, sorghum, millet, rye, soybean, sunflower, safflower, alfalfa, canola Brassica napus, cotton, or turf grass.

Seeds derived from plants regenerated from transformed plant cells, plant parts or plant tissues, or progeny derived from the regenerated transformed plants, may be used directly as feed or food, or further processing may occur.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Identification of Candidate IPP2-K Genes

DNA sequences for predicted inositol pentakisphosphate-kinase (In5-K) genes from human and yeast were described in Verbsky, J. W. et al. (2002) J. Biol. Chem. 277: 31857-31862 (hereinafter "Verbsky"). Fragments of similar, putative maize IPP2-K gene sequences were identified in public databases including GenBank (http://www.ncbi.nlm.nih.gov/). The maize sequence fragments were aligned with human and yeast sequences, and also used for NCBI database searching according to BLAST algorithms (Altschul, S. F. et al. (1991) J. Mol. Biol. 215:403-10). Several sequences from *Arabidopsis thaliana* (AT5g42810, AT1g22100, AT1g58936) and other species were identified in the public domain including, but not limited to BM520171, BE556094, BG882429 (*Glycine max*); C73039, AA750614, AL606608.3, AAAA01003483, AP008210, AK102842, XM 474214 (*Oryza sativa*); BH647760, BH724856 (*Brassica oleracea*); TC238218 (TIGR contig comprising ESTs CA732984, BQ579364, BE430881, CD876080, BE498028, CA714664, BE498127, BJ233635, BE496998, CA604588, BJ212905, BJ220381, BE445478, CA700172, CA613702 from *Triticum aestivum*), TC97085 (TIGR contig comprising CD233879, BG054179, BE594569, CD207152 from *Sorghum bicolor*), BN45053K04, BN25068E01, Brassica_napustuc04-02-05_2912, TC1941 (TIGR contig comprising CD832483, CD827663, CD837809 and CD832284 from *Brassica napus*).

Figure 1B:
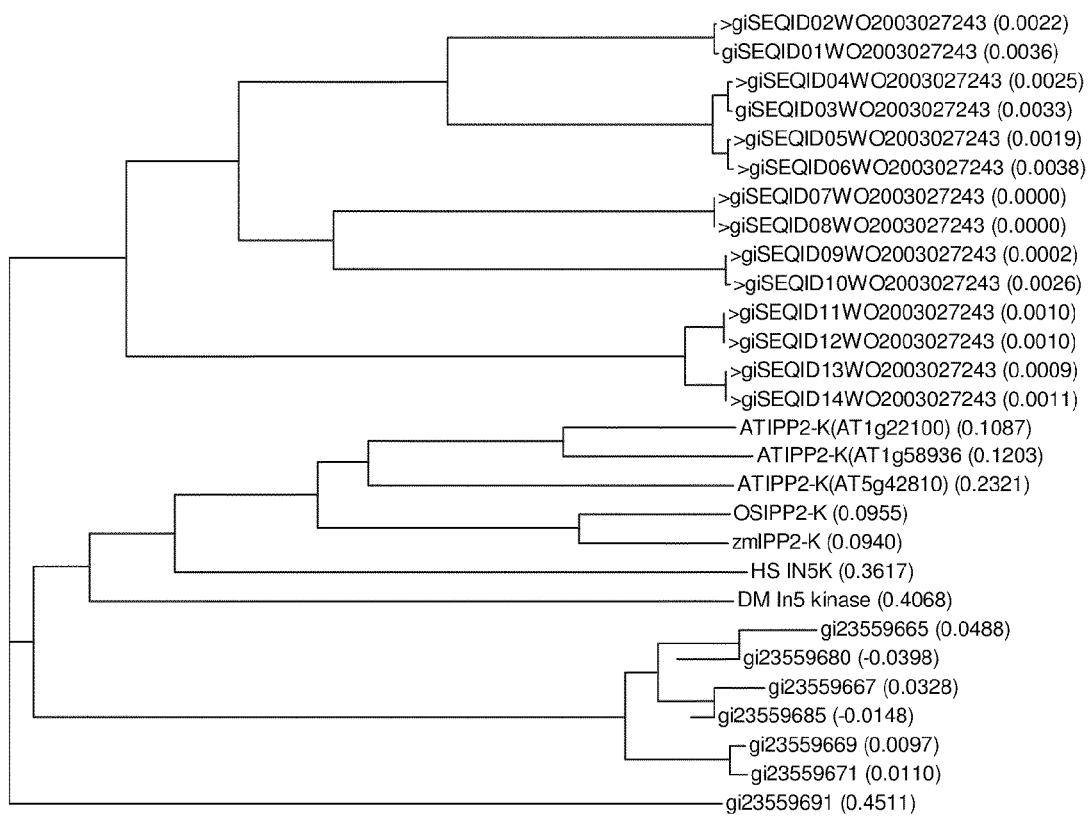

In addition, sequences that have low levels of sequence similarity and are predicted to be functionally distinct were identified in public databases and published patents applications (Shi, J. et al WO2003027243). These sequences may be differentiated from those similar to IPP2-K claimed herein on the basis of the degree of similarity. The percentages of similarity and phylogenetic relationships between these sequences are shown in FIGS. 1A and 1B.

In addition, Multiple Sequence Alignment applications of Vector NTI were used to create alignment of the predicted amino acid sequences of putative IPP2-K genes from maize, Arabidopsis and rice. Based on amino acid sequence identity, the results of those alignments defined conserved regions that are designated as consensus sequences as diagrammed in FIG. 2. Five consensus sequences were determined to define motifs that are characteristic of IPP2-K genes. Using these motifs to search databases (e.g. GeneBank), one practiced in the art may identify additional putative IPP2-K genes from a variety of plant species:

1: DAXDWXYXXEGXXNLXLXYXGSSP

2: VEIKXKCGFLXXSXXIXXXNXXKXXXXRXXMXQXCKXXXXXISXXS EYXPLDLFSGSKXXXXXAIKXXXXTPQNXXXXXXGSLXXGG

3: ISXXSEYXPLDLFSGSK

4: LXXLLXXQKLDXXIEGXIHXYY

5: LIXXTAXDCSXMISF

Example 2

Isolation of Full-Length cDNA Sequences

Searches of the public maize sequence database (www.maizegdb.org) identified expressed sequence tags (ESTs) BG842305, AW066374 and BE639260 as fragments of contiguous sequence (contig) ZMtuc02-12-23.4536. This contig is 1.7 kb in length. The translated protein sequence of this contig contains sequences that were highly similar to the conserved A, B, C and D boxes identified in the human inositol pentakisphosphate kinase (In5-K) gene as described by Verbsky. An RT-PCR approach was used to obtain maize IPP2-K cDNA clones as described in this example.

Poly(A)+-tailed mRNA was isolated from maize (DAS 5XH751) seeds at 9 days after pollination (DAP) using a combination of TRIzol reagent (Invitrogen, Carlsbad, Calif.) and a MACS kit (Miltenyi Biotec, Auburn, Calif.). A reverse-transcription reaction was performed on this mRNA to generate cDNA using a gene specific primer derived from ZMtuc02-12-03.4536 (5'-TCG GAA ATT ACT GTG ACA AGC-3') and Superscriptase II enzyme (Invitrogen) as suggested by the manufacturer. Amplification of an IPP2-K cDNA was accomplished by using different gene-specific primers derived from ZMtuc02-12-23.4536 (5'-GAA TCG GCA CGA GGC AGC AGC GGC AGC-3' and 5'-TGA CAA GCC ACG GTG TAT GCA-3'). The amplified cDNA was cloned into vector plasmid vector pCR2.1 using a TA cloning kit as per the manufacturers recommendation (Invitrogen). This maize IPP2-K cDNA clone (1.6 kb in length) was designated as zmIP5K-1.

To obtain sequences corresponding to the 5'- and 3'-untranslated regions (UTRs) of the IPP2-K cDNA, rapid amplification of cDNA ends (RACE) experiments were performed using the GeneRacer™ kit from Invitrogen. For 5'-RACE, the mRNA from seed at 9 DAP was treated with calf intestinal phosphatase and tobacco acid pyrophosphatase as described by the manufacturer. An RNA oligonucleotide (RNA anchor) supplied with the kit was ligated to the mRNA described above as per kit instructions. Reverse transcription was directed by another IPP2-K gene-specific primer (5'-GCA ATA GCA AAT TGA GAT ACA TTC ATA C-3'). The 5'-end of the putative maize IPP2-K kinase cDNA was subsequently amplified using a primer derived from the sequence of the RNA anchor and a different gene-specific primer (5'-TTC CAG GCG TTA AGG GTC GAG CCT-3'). The resulting amplicon was cloned into plasmid vector pCR2.1 and sequenced.

To obtain 3'-UTR sequences, reverse transcription of mRNA from 9 DAP-seed was directed with an oligo-d(T) primer and a primer derived from the RNA anchor at the 3'-end as per the GeneRacer™ kit. The 3'-ends of putative IPP2-K transcripts were then amplified with gene specific primers derived from zmIP5K-1 (5'-CGT GTT TCT AGG GAT TTT CTG GAG CTT-3') and from the 3'-RNA anchor sequence flanking the oligo-d(T) primer. The PCR products were cloned into pCR2.1 and sequenced. Subsequently, sequence data of clones derived from both 5'- and 3'-RACE experiments were used to design IPP2-K specific PCR primers corresponding to the UTRs (5'-CTT CAG TCC CTT TCC CCG GGC T-3' and 5'-TTT TTT TTT TTT GGA GGA TGA AAG TTT CAC CAA ACA TTT CT-3'). Using those primers, RT-PCR amplification of mRNA from 9 DAP seeds was performed using Platinum Taq DNA Polymerase High Fidelity (Invitrogen) to yield putative full-length IPP2-K cDNAs. The resulting PCR products were then cloned into pCR2.1 and four independent clones were sequenced. The nucleotide sequence of the clone representing the full-length IPP2-K cDNA is designated as (SEQ ID NO 1) and the predicted amino acid sequence of the protein encoded by this cDNA is designated as (SEQ ID NO 2).

Example 3

Identification of Genomic DNA Sequences

Using the sequence of the isolated putative maize IPP2-K cDNA as a query, the maize genomic database (www.maizegdb.org) was searched according to BLAST and additional overlapping, similar sequence fragments of unknown function were identified. These sequences were assembled into contigs/singlets including ZMGSS-tuc28403.1, ZMGSStuc 03-04-29.4761.

Genomic Southern blots were carried out using standard protocols (Sambrook). Maize (DAS 5XH751) genomic DNA was analyzed either undigested or digested singly with BamH I, EcoR I, Hind III and Not I enzymes. The gDNA fragments were separated by electrophoresis in 0.8% agarose, transferred to a nylon membrane and hybridized under stringent conditions (0.2×SSC, 60° C. degrees) with 25 ng of 1.6 kb maize IPP2-K cDNA (zmIP5K-1) probe labeled with $^{32}$P-dCTP (Prime-It II labeling kit, Stratagene, La Jolla, Calif.). Bands corresponding to 2 or 3 genes were identified as possible IPP2-K candidates, indicating the gene is present as a small gene family.

Example 4

Isolation of IPP2-K Genomic Clones from a Lambda Phage Library

Genomic DNA from maize (DAS5XH751) was isolated from 3-week old leaf tissue that had been ground to a fine powder in liquid nitrogen. gDNA was extracted using standard cetyltrimethylammonium bromide-based methods (CTAB) as described in Sambrook in a buffer consisting of 100 mM Tris pH7.5, 0.7M NaCl, 10 mM EDTA, 1% CTAB, 1% β-mercaptoethanol. The resulting DNA was digested with BamH I restriction enzyme and the ends were subjected to a fill-in reaction using Klenow enzyme (Stratagene, La Jolla, Calif.) as per the manufacturer's recommendations. Following the fill-in reactions, the DNA was extracted, precipitated and ligated into a lambda bacteriophage vector (Lambda FixII, Stratagene) which was predigested with Xho I according to the protocol described by the manufacturer except that the ligation buffer and ligase enzyme were provided by Promega (Madison, Wis.). Using the Gigapack kit from Stratagene, the ligation mix was added to Gigapack III XL packing extract as per the manufacturer's recommendations and the packaged library was plated onto LB media using standard methods described by Sambrook. The resulting maize genomic library had a phage titer of $3.6 \times 10^6$ PFUs. Following routine amplification, the final titer of the library was $3.6 \times 10^{10}$ PFU/ml.

Methods for lambda library screening were derived from Sambrook. The maize DAS5XH751 genomic library was plated at a high density and transferred to nylon membranes. The membranes were hybridized under stringent conditions (2 washes 1×SSC, 2 washes 0.2×SSC at 65° C.) with a probe consisting of a 1.6 kb IPP2-K cDNA clone (zmIP5K-1) fragment labeled as described above. Positive plaques were isolated and subjected to 2 additional rounds of screening, resulting in several putative positive lambda clones. DNA sequencing of the cloned fragments confirmed the identity of these sequences as derived from the genomic IPP2-K gene. These sequences along with BAC clones described below were used to generate the contiguous genomic sequence designated as (SEQ ID NO 3).

Example 5

Isolation and Characterization of a BAC Clone Containing IPP2-K Gene

A bacterial artificial chromosome (BAC) library of genomic DNA from maize (DAS inbred 5XH751) was prepared according to methods described by Zhang (2002).

Leaf tissue was harvested from 2-week old seedling tissue and frozen in liquid nitrogen. Frozen tissue was ground into fine powder in liquid nitrogen, transferred into 1XHB (10× stock: 0.1 M Trizma base, 0.8 M KCl, 0.1 M EDTA, 10 mM spermidine, 10 mM spermine, pH 9.4-9.5) plus 0.15% β-mercaptoethanol and 0.5% Triton X-100, swirled for 10 minutes on ice and filtered through two layers of cheesecloth and one layer of Miracloth. The homogenate was pelleted and washed with ice cold wash buffer (0.01 M Trizma base, 0.08 M KCl, 0.01 M EDTA, 1 mM spermidine, 1 mM spermine, 2% Triton X-100, 0.015% β-mercaptoethanol, pH 9.4-9.5). The nuclei pellet was resuspended in wash buffer and re-pelleted by centrifugation at 1,800×g, 4° C. for 15 minutes 3 times. Pelleted nuclei were resuspended in 1 ml of 1XHB and counted. Nuclei concentration was adjusted to $5 \times 10^7$ nuclei/ml with 1XHB. Intact nuclei were embedded in agarose plugs as described in Zhang (2002), washed in 0.5 M EDTA, pH 9.0-9.3 for one hour at 50° C., washed in 0.05 M EDTA, pH8.0 for one hour on ice, and stored in 0.05 M EDTA, pH8.0 at 4° C. Further purification of megabase DNA in the plugs was performed by washing the nuclei-plugs three times for one hour in 10-20 volumes of ice cold TE (10 mM Tris-HCl, pH8.0, 1 mM EDTA pH 8.0) plus 0.1 mM phenylmethyl sulfonyl fluoride (PMSF). The DNA was additionally washed three times for one hour in 10-20 volumes of ice cold TE.

Genomic DNA in embedded nuclei was digested with restriction enzyme EcoRI directly in the agarose plugs as described in Zhang (2002). Following digestion, the reactions were stopped with 1/10 volume of 0.5 M EDTA, pH 8.0. Pulsed-field gel electrophoresis followed by size-selection in agarose plugs was carried out on digested DNA prior to ligation in BAC vectors according to Zhang (2002).

As described in Zhang (2002), BAC vector pECBAC1 DNA was digested with restriction enzyme EcoRI. Linearized vector DNA was dephosphorylated with CIAP enzyme (Invitrogen) and the 400 ul reaction was stopped with 4 µl 0.5M EDTA, pH 8.0, 20 µl 10% SDS and 40 µl 1 mg/ml proteinase K in cold TE. DNA was precipitated by adding 1/10 volume of 3 M NaAC, pH 7.0 and 2 volumes of 100% ethanol, incubating at −80° C. for 10 minutes followed by centrifugation at 10,000 rpm for 15 minutes. After washing and resuspension, the DNA concentration was adjusted to 10 ng/µl and vector was stored at −20° C.

Ligation of megabase genomic DNA into BAC vector pECBAC1 was carried out as follows: genomic DNA eluted from the agarose plug was dialyzed 2× against one liter of ice-cold 0.5×TE on ice, for 1 hour. The concentration of collected DNA was estimated on a 1% agarose gel. Ligation reactions were performed at a vector:DNA molecular weight ratio of 1:4 with T4 DNA ligase enzyme according to standard procedures as described in Zhang (2002). The ligation reactions were incubated at 16° C. for 8-12 hours.

Transformation of ligation mixtures into competent *E. coli* cells (DHB10B, Invitrogen) was performed via electroporation using a Cell Porator System with Voltage Booster and 0.15 cm gap Cell Porator cuvettes (Labrepco, Horsham Pa.). Electroporation settings were 330 uF capacitance, 4K ohms resistance. Following electroporation, cells were recovered at 37° C. with shaking in ~1 ml of SOC media, pelleted with centrifugation and stored in freezing media (2.5 w/v granulated LB broth, 13 mM $KH_2PO_4$, 36 mM $K_2HPO_4$, 1.7 mM sodium citrate, 6.8 mM $(NH_4)_2SO_4$, 4.4% w/v glycerol) until plating. Cultures were plated on LB media plus 1.5% bactoagar, 90 ug/ml X-gal, 90 ug/ml IPTG and 12.5 ug/ml chloramphenicol at a density that resulted in discreet bacterial colonies. Individual colonies were picked using a Q-bot robot (Genetix, Boston Mass.) picking routine and arrayed into 300 384-well plates. Titer testing of this corn BAC library derived from inbred variety DAS 5XH751 indicted the library contained approximately 115,000 clones with an average insert size of 130 kb genomic fragments.

Figure 3:
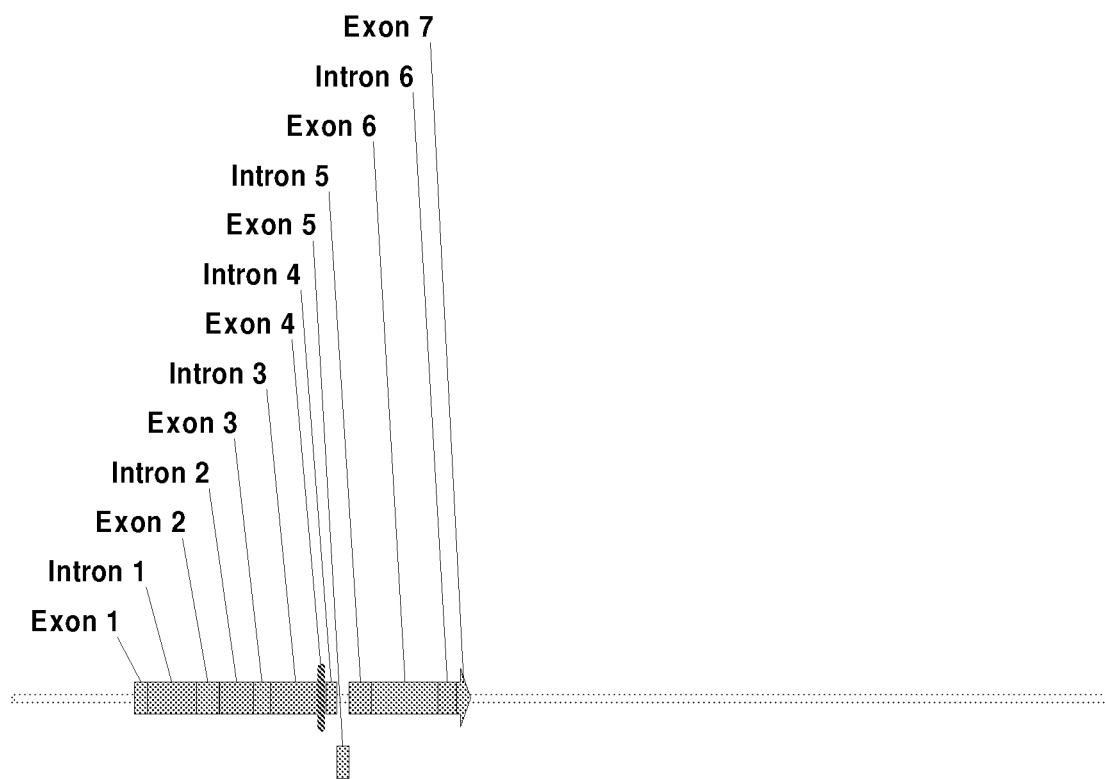
FIG. 3 shows the gene organization of IPP2-K from maize inbred line DAS 5XH751.

The arrayed maize 5XH751 BAC library was spotted onto 22 $cm^2$ nylon membranes in 4×4 grids using a Q-bot robot (Genetix, Boston Mass.) spotting routine. Filters were grown on LB agarose at 37° C. overnight, then denatured, fixed and dried as per Sambrook except that an additional lysis step was added, prior to hybridization. The filters were hybridized under stringent conditions (2 washes 1×SSC 0.1% SDS, 2 washes 0.2×SSC, 0.1% SDS at 65° C.) with a probe consisting of a 916 bp IPP2-K fragment (zmIP5K-1) generated by PCR of cDNA clone (zmIP5K-1) using IPP2-K specific primers (IP5K-PF3: 5'-AGTCCCTTTCCCCGGGCTGTGG-TAC-3' and IP5K-PR1: 5'-TTAAGTTGTTCTGAGGAGT-TGAGAAAAGGGA-3'). Probe was radio-labeled with $\gamma^{32}$-P dCTP using a random primer labeling kit from Invitrogen. Visualization of positive clones was carried out via phosphorimaging for a 16-hour exposure with storage-phosphor screens followed by Storm phosphorimager (Molecular Dynamics, Mountain View Calif.) analysis running Incogen (Williamsburg, Va.) High Density Filter Reader software. Positive clone cultures were retrieved from the library plate array and grown overnight at 37° C. in LB media. BAC DNA was extracted from isolated clones using a Qiagen (Valencia Calif.) Large Construct kit as per the manufacturers instructions. PCR primers specific for coding regions of IPP2-K (IP5-IPF: 5'-CGCGGATGCCAAGGACTGGGTTTA-CAAGGG-3' and IP5-IPR: 5'-TTACAACAGCAGCAC-CAAGCAGCAGGAAC-3') were used to amplify putative positive clones and confirm the presence of the IPP2-K gene on the BAC. BAC clones containing the IPP2-K genes were restricted with NotI, subjected to pulsed-field gel electrophoresis and analyzed. The insert size was estimated to be approximately 180 kb in length, corresponding to the genomic region of maize chromosomes containing the IPP2-K gene. Sequencing of the IPP2-K containing BAC clone was carried out either through direct sequencing of BAC DNA or via shotgun-subcloning of the BAC followed by plasmid sequencing and contig assembly (Lark Technologies, Houston Tex.). Multiple BAC sequence runs were generated and aligned with lambda phage clone sequences described above to derive the contiguous genomic sequence designated as (SEQ ID NO 3). The structure of the genomic loci containing the IPP2-K gene from maize DAS 5XH751 is shown in FIG. 3.

Example 6

Characterization of IPP2-K Activity In Vitro

A fragment of the maize IPP2-K cDNA clone corresponding to the predicted open reading frame (ORF) of 1.32 kb was cloned into the pGEX-2T plasmid expression vector (Amersham Pharmacia Biotech, Piscataway, N.J.) and expressed in *E. coli* cells (BL21(DE3) pLysS) as per the manufacturer's recommendation. This vector is designed to generate an inframe fusion of GST (glutathione-S-transferase) peptide onto the N-terminus of the expressed protein.

Total protein was extracted from the *E. coli* cells in a standard extraction lysis buffer (50 mM Tris-HCl pH7.5, 150 mM NaCl, 10 mM EDTA, 1 mM DTT, 1 mM PMSF, 1 mg/ml lysozyme followed by addition of 0.4% Triton X-100). The resulting *E. coli* lysate was sonicated on ice using a Branson Sonifier 450 (Branson Ultrasonic Corporation, Danbury Conn.) for four cycles of 30-seconds each with a 20% output setting and 50% duty cycle. The bacterially expressed protein was passed over a glutathione-agarose column, washed 3× with buffer A (50 mM Tris-HCl pH7.5, 150 mM NaCl, 10 mM EDTA, 1 mM DTT, 1 mM PMSF and 0.4% Triton X-100), 3× with buffer B (50 mM Tris-HCl, pH 8.0) and eluted with 10 mM glutathione in 50 mM Tris-HCl. 0.5 ml fractions containing proteins as determined by Bio-Rad (Hercules Calif.) protein assay reagent were pooled and analyzed by SDS-PAGE (Sambrook). The identity of the heterologously expressed, purified protein was confirmed to be maize IPP2-K using peptide fragment fingerprinting methods as described by Shevchenko, A. et al. (1996) Anal. Chem. 68:850-858.

Figure 4:
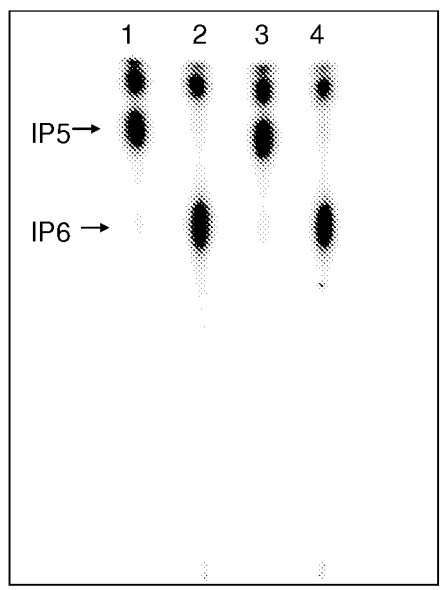
FIG. 4 shows the in vitro kinase activity of maize IPP2-K using $^{32}$P-γATP, IP4 and IP5 substrates as detected with radiolabeled substrate and TLC. IPP2-K converts inositol 1,4,5,6-tetrakisphosphate into inositol pentakisphosphate, and converts inositol 1,3,4,5,6-pentakisphosphate into phytate (inositol hexakisphosphate).

The ability of the heterologously expressed maize IPP2-K protein to phosphorylate multiple inositol-phosphate species, including inositol tetrakisphosphate (IP4) and inositol pentakisphosphate (IP5), was confirmed by autoradiography after $^{32}$-P labeled inositol phosphates were separated with conventional thin layer chromatography (FIG. 4.). Maize IPP2-K activity assays of the purified protein were carried out in a reaction buffer containing 20 mM HEPES (pH7.5), 6 mM MgCl$_2$, 10 mM LiCl, 1 mM DTT, 40 ng/μl inositol phosphate substrates, 40 μM ATP and 5 μCi of γ-$^{32}$P labeled ATP (3000 Ci/mmol). The reaction mixes were spotted onto a PEI cellulose TLC plate and developed in 1.0 N HCl. Results of these kinase activity assays indicated that the maize IPP2-K enzyme was able to catalyze the conversion of inositol 1, 3, 4, 5, 6 pentakisphosphate (IP5) to generate inositol 1, 2, 3, 4, 5, 6 hexakisphosphate (phytic acid) via a phosphorylation reaction at the 2-position of the inositol ring (FIG. 4). In addition, this maize enzyme was able to phosphorylate inositol 1, 4, 5, 6 tetraIphosphate (IP4) to produce IP5. Additional observed activity of the enzyme included the ability to convert inositol 1,4,6-triphosphate (IP3) into a radioactively labeled IP3 product. Based on these results, the maize enzyme is an inositol polyphosphate kinase.

To further characterize the isomeric specificity of the inositol 1,4,6-triphosphate kinase activity of IPP2-K observed in the TLC assay described above, an NMR-based approach was utilized to examine substrate conversion. In this example, a solution containing 600 ul, 50 mM Tris DCl, pH 7.5, 10 mM LiCl, 6 mM MgCl$_2$, 1 mM DTT, 1 mM inositol 1,4,6-triphosphate, and 1 mM ATP in D$_2$O was placed in a 5-mm NMR tube and analyzed by proton NMR on a Bruker DRX-600 NMR. Data was collected using a RECUR-TOCSY pulse sequence in order to eliminate the large residual water peak at 4.8 ppm while retaining the substrate peaks lying underneath according to the method of Liu el. al (2001). After characterization of the starting materials, 45 ug of purified heterologously expressed maize IPP2-K enzyme was added to the tube and the reaction monitored as before using proton NMR. All spectra were obtained at room temperature at a proton resonance frequency of 600 MHz. A total of 128 scans were used with 32K data points, a 30 degree pulse width, and 2 second relaxation delay. Data collection and processing was carried out using the standard Bruker software XWIN-NMR. Spectra representing time points 0 and 120 minutes incubation at 37° C. in the presence of enzyme are shown in FIG. 5. Comparison of spectra from start and end time points indicates that in the presence of IPP2-K enzyme, inositol 1,4,6-triphosphate is converted to inositol 1,2,6-triphosphate (FIG. 5). This result clearly demonstrates that IPP2-K can catalyze both the dephosphorylation and phosphorylation of inositol 1,4,6-triphosphate as observed in the TLC assays; furthermore, the kinase activity of IPP2-K is specific for phosphorylation at the inositol-2 position, confirming that the enzyme encoded by the IPP2-K gene is an inositol polyphosphate-2 kinase.

Example 7

Characterization of IPP2-K Activity In Vivo

The functionality of the protein encoded by the isolated IPP2-K cDNA from maize DAS 5XH751 may be tested by genetic complementation experiments. In one example, mutants of the dicotyledenous plant *Arabidopsis thaliana* containing alterations in the IPP2-K gene may display a reduced phytic acid accumulation phenotype. For example, one may identify publicly available *Arabidopsis* lines described as containing T-DNA insertions in the predicted IPP2-K gene by searching the TAIR database (www.*arabidopsis*.org) using the maize IPP2-K cDNA sequence as a query. Lines containing such T-DNA insertions may exhibit decreased or knocked-out expression of the interrupted IPP2-K gene, resulting in decrease or loss of enzyme activity. Seeds from the self-pollinated progeny of those lines may be subjected to analysis of phytate content using a chelating assay described by Raboy in U.S. Pat. No. 6,111,168A. It is predicted that disruption of the *Arabidopsis* IPP2-K gene, which is homologous to the maize IPP2-K gene, and resulting elimination of IPP2-K activity, may lead to a reduction in phytate accumulation. It is predicted that when such plants are engineered via genetic transformation as described in Weigel, D. & Glazebrook, J. (2002) *Arabidopsis A Laboratory Manual* (Cold Spring Harbor Laboratory Press, Cold Spring Harbor, N.Y.) to express a functional maize IPP2-K gene, these mutant lines may recover normal, near-normal or increased levels of phytic acid accumulation.

In another example similar to the *Arabidopsis* experiments described above, one skilled in the art may identify mutants of maize from publicly available genetic collections such as (http://www.uniformmu.org; or http://w3.aces.uiuc.edu/maize-coop/) that are disrupted in the IPP2-K gene. For example, some mutants of maize may be disrupted in the IPP2-K gene because of the presence of a Mu transposable element inserted into the gene. It is predicted that these mutants may exhibit reduced levels of phytic acid accumulation. Such mutants may be complemented by expressing the functional maize gene via genetic transformation. When such plants are engineered via genetic transformation to express the maize IPP2-K gene, it is predicted that these mutant lines will recover normal or near-normal levels of phytic acid accumulation.

In the examples cited above, one skilled in the art may utilize NMR analysis to determine the specific amount and type of inositol phosphate metabolites present in the genetically altered plants. Plants exhibiting decreased accumulation of phytic acid due to alteration of IPP2-K gene expression are predicted to also have altered amounts and/or types of phytate precursors such as IP5, IP4 etc. For example, plant extracts from such mutants may be analyzed using phosphorous NMR to determine the effect of phytate reduction on the accumulation of phytate precursors. To illustrate this example, a determination of the inositol phosphate molecules present in mature maize seed from inbred line DAS 5XH751 was carried out. In this example, 10 g of corn flour from dried, mature maize seed was extracted in 0.5N HCl, filtered, concentrated to dryness and washed with 80% methanol. The methanol slurry was concentrated to a black tar and dissolved in a D$_2$O solution containing 30 mg/ml EDTA. Solution pH was adjusted to >12 with NaOH. Phosphorous NMR analysis was subsequently performed without filtration. Phosphorous NMR spectra were obtained at 400.13 MHz on a Bruker DRX-400 NMR spectrometer fitted with a 5-mm 1H/13C/19F/31P probe. All spectra were obtained with proton decoupling at room temperature. A total of 23K transients were obtained using 64K data points, a 30 degree pulse width and a 2.0 second relaxation delay resulting in total acquisition time of 16 hours. The raw data was zero-filled to 32K points spectra and processed using a 1.0 Hz exponential weighting function. The resulting spectrum is shown in FIG. 6. In non-mutated maize, it is predicted that inositol hexakisphosphate (phytate) is the predominant inositol phosphate species, with small amounts of inositol penta- and tetra-kisphosphates present, as observed in FIG. 6.

Example 8

Mutagenesis of Maize Seed Using Fast-Neutron (FN) Irradiation

The methodologies and general genetic consequences of FN bombardment of cells are well described by van Harten (1998), and this method has been successfully used on *Arabidopsis* plants as described by Li, X. et al. (2001) Plant J. 27: 235-242. FN can typically be expected to produce deletions in the approximate size range of a few hundred base pairs to several thousand base pairs or more. The efficacy of FN irradiation is dependent on the type and quality of biological material subjected to treatment. In this example, irradiation was carried out using a fast-neutron beam source at the Atomic Energy Research Institute in Budapest, Hungary. In one experiment to mutagenize a maize seed sample, bulk seed that had been dried to appx. 40% moisture post-harvest was tested for water content prior to irradiation by measuring mass before and after treatment for 14 h at 80° C. in a laboratory drying oven. Based on the sample % water w/w, the actual calculated beam exposure time was adjusted according to the instrument beam calibration. For these samples, an irradiation geometry at BIF of BRR of 2Y/Cd rotating geometry was applied. Exposures were monitored by U-235, Th-232 fission chambers and a GM counter. Irradiation exposures were carried out on individual packets of seed for 1145 seconds each to yield an actual averaged kerma dose rate for 2Y/Cd of 12.71 mGy/s+3%. Multiple maize seed samples were treated with a targeted dose range of 11-20 Gy (11, 13, 15, 17, 20 Gy) of fast neutrons. The resulting M1 seeds were planted and grown under standard midwestern field conditions, open pollinated and each M1 ear was harvested individually to produce an M2 family. Individual mature ears were collected, dried, shelled and packaged into individual envelopes labeled with M2 family-specific identifiers.

Example 9

Isolation of Genomic DNA from Mutagenized Seed

Genomic DNA was isolated from whole, dried maize seeds in a 96-well format using the Charge-Switch Technology (CST) method from Invitrogen (Carlsbad, Calif.) with the following modifications. Seed samples from each M2 family were individually removed from envelopes for genomic DNA extraction. 6 seeds from each family were placed in each well (1 family per well) of a 24-well deep well plate (CoStar Scientific, Cambridge Mass.), imbibed in water overnight and subsequently lyophilized in a freeze-dry chamber (Virtis, Gardiner N.Y.) under vacuum for a minimum of 48 hours. Dried seeds were ground to a powder using a Genogrinder (Spex Certiprep, Metuchen N.J.) at maximum setting in combination with tungsten-carbide beads (Small Parts, Inc., Miami Lakes Fla.) and resuspended in aqueous buffer consisting of 0.25% SDS, 10 mM EDTA pH8.0, 50 mM Tris pH8.0. Following centrifugation, extract supernatant was transferred to a new plate and pooled to a combination of 6 samples (M2 families) per well. Proteins were precipitated from solution by addition NaCl to 750 mM and KOAc to 1.2 M final concentration on ice followed by brief centrifugation. PEG8000 was added to the supernatant to a final concentration of 8%, mixed and centrifuged to pellet the gDNA. Pellets were resuspended in CST (Invitrogen) digestion mix and gDNA was extracted as per the manufacturer's protocol using a Biomek FX robotic liquid handling system (Beckman-Couter, Inc., Fullerton Calif.). Following elution, DNA samples were aliquotted into multiple sealed plates and stored either at −80° C. or 4° C. in a moisture container.

Example 10

PCR-Based Screening for Deletion Mutants

In order to screen for deletions in a target gene, a PCR-based method may be applied. Examples of several such methods are described in US patent application 20050053975. For example, oligonucleotide primers corresponding to genomic sequence flanking the gene of interest may be designed based on sequence data for the locus. DNA samples may be subjected to PCR amplification using commercially available methods and enzymes (LA-Taq) optimized for long PCR as per the manufacturer's recommendations (Takara-Bio, Inc., Shiga, Japan). Detection of deletions may be carried out by routine agarose-gel electrophoresis (Sambrook) to visualize PCR product bands. To illustrate the utility of this method, oligonucleotide primers that correspond to genomic DNA sequence flanking a maize Adh-1 locus were designed based on published information. These primers were used to amplify maize genomic DNA under the following conditions: reaction mixtures containing 1×LA-Taq buffer, 1.6 mM dNTPs, 0.5 mM $MgCl_2$, 2% DMSO and LA-Taq enzyme were added to gDNA template (1-30 ng) and 0.4 µM oligonucleotide primers (primer Adh16s: 5'-GTCT-GACAACGCCTGAGATTGAATCGAAGACC-3', primer Adh21a: 5'-CAGCTACCACTTGCGCTTGAGG-GATTTGAA-3'). The PCR reaction was amplified under the following temperature regime in an automatic thermocycler (MJ Research, Waltham, Mass.):

Step 1: 94° C. for 1 minute; Step 2: 98° C. for 10 seconds; Step 3: 70° C. for 15 minutes; Step 4: repeat steps 2 & 3 for an additional 31 cycles; Step 5: 72° C. for 10 minutes; and Step 6: 4° C. hold for storage.

Resulting PCR products were analyzed using conventional agarose gel electrophoresis. The amplicon thus generated encompassed the entire Adh-1 gene plus several kb of flanking sequence, for a total of 12.3 kb of DNA sequence. In the event that the template gDNA used in such a reaction contains a deletion within that 12.3 kb span, one may detect a smaller PCR product, which indicates a mutation in the source germplasm. We have applied this method to several other genes of interest. As shown in these examples, one practiced in the art may detect PCR reactions showing amplicons of reduced size relative to controls. The seed source of the DNA template used in these reactions may be designated as a putative deletion mutant and subjected to repeated analysis. Once the deletion is confirmed, mutant maize from that family may be grown and self-pollinated to generate homozygous germplasm. Phytate levels in seeds from such germplasm may be measured in 10 to 20 M3 seeds using conventional assays for detection of phytic acid as described by Raboy supra. Seed containing reduced phytate may be regrown and tested for enhanced nutritional value in animal feeding trials or other uses.

REFERENCES

Altschul, S. F. et al. (1991) J. Mol. Biol. 215:403-10
Guthrie, C. & Fink, G. (1991) *Guide to Yeast Genetics and Molecular Biology*. Meth. Enzymol. v194. Academic Press, Inc., San Diego, Calif.
Ives, E. B. et al. (2000) J. Biol. Chem. 275: 36575-36583
Li, X. et al. (2001) Plant J. 27: 235-242
Liu, M. et al. (2001) *J. Magn. Reson.* 153, 133-137
Raboy, V. (2000) *Low Phytic Acid Mutants and Selection Thereof*, U.S. Pat. No. 6,111,168 Assignee: The United States of America as represented by the Secretary of Agriculture, Washington, D.C.
Sambrook, J. & Sambrook, D. W. (2001) *Molecular Cloning A Laboratory Manual*. Cold Spring Harbor Laboratory Press, Cold Spring Harbor, N.Y.
Shevchenko, A. et al. (1996) Anal. Chem. 68:850-858
Shi. J., et al. (2003) *Phytate Polynucleotides and Methods of Use*. International patent application #WO2003027243. Applicant: Pioneer Hi-Bred International, Inc., USA
van Harten, A. M. (1998) in *Mutation Breeding Theory and Practical Applications*. Cambridge University Press, Cambridge, UK.
Verbsky, J. W. et al. (2002) J. Biol. Chem. 277: 31857-31862
Weigel, D. & Glazebrook, J. (2002) *Arabidopsis A Laboratory Manual*. Cold Spring Harbor Laboratory Press, Cold Spring Harbor, N.Y.
Zhang, H.-B. (2002) *Construction and Manipulation of Large-Insert Bacterial Clone Libraries Manual*. Department of Soil and Crop Sciences and Crop Biotechnology Center, Texas A&M University. available online: http://hbz7.tamu.edu/index.htm All publications, patents, patent applications and computer programs cited in this application are herein incorporated by reference to the same extent as if each individual publication or patent application was specifically and individually indicated to be incorporated by reference.

```
                                                                    SEQ ID NO. 1
   1 cttcagtccc tttccccggg ctgtggtacc agtactagta ccagcatctc ttcaggctcc
  61 accaagcgca gacaccgcag cagcggcagc ggcacgatct ggtgaccccc cgccgcgtca
 121 agcctgctcc tccggtgatc gccggactgg cggggtagga accagcggag cgcagcccgc
 181 ctccttccgc tgcagaagat cctcgatgga gatggatggg gttctgcaag ccgcggatgc
 241 caaggactgg gtttacaagg gggaaggcgc cgcgaatctc atcctcagct acaccggctc
 301 gtcgccctcc atgcttggca aggtactgcg gctcaagaag attctaaaaa acaagtcgca
 361 gcgggcaccg agttgtattg tattctcaag tcatgagcaa ctcctgtggg gccatatccc
 421 agaactggtt gagtcggtca aacaagattg cttggctcaa gcctatgcag tgcatgttat
 481 gagccaacac ctgggtgcca atcatgtcga tggtggggtc cgtgtacgtg tttctaggga
 541 ttttctggag cttgtcgaaa agaatgttct tagcagccgt cctgctggga gagtaaatgc
 601 aagttcaatt gataacactg ctgatgccgc tcttctaata gcagaccact ctttattttc
 661 tggcaatcct aagggtagca gctgcatagc tgtagagata aaggccaaat gtgggtttct
 721 gccatcatca gaatatatat cagaagataa tactatcaag aaactagtaa cgagatataa
 781 gatgcatcag cacctcaaat tttatcaggg tgagatatcg aagactagtg agtacaatcc
 841 tcttgatcta ttttctgggt caaaagagag aatatgcatg gccatcaagt ccctttctc
 901 aactcctcag aacaacttaa ggattttgt caatggatct ttagcttttg gtggcatggg
 961 aggtggtgca gatagtgttc atcctgctga cactcttaag tgtcttgaag atctcagcaa
1021 gattagtggc ctaaaactcc ctgacttcac tgagctcctg tcagagacaa tttttaggtc
1081 tgaggtatta ggcaacctgt tggccactca aaagctggat gatcatgaca ttgaaggggt
1141 aattcatctg tactacaaca taatttctca gccttgttta gtctgcaaaa acctaactga
1201 tgtagagcta ttgcggaagt acactttctt gcattctctt ccgttggaca aaagcctgaa
1261 gatcgttagg gacttcctca tttctgctac cgcaaaggac tgtagcctga tgatcagctt
1321 tcggccaaga gagaatggta gtacagattc tgagtatgat tcagtgtttc ttgaatcagc
1381 gaagcgaacc tatgagtaca aggcatattt ccttgatctg gatgtgaaac ctctggataa
1441 gatggagcat tattttaaac tggatcagag gatagtcaat ttctacacaa gaaatggggg
1501 aggtcttgcc atctccaaag ggcagtaata ccaaagacac ttcgaggatt cagctccaag
1561 aacggggagc ctctcttcct gtatacatct ggagaagggt gcatcaggga gtgttggttg
```

-continued

```
1621  ttgttcctgc tgcttggtgc tgctgttgta acttcatgag tacagtccca aggttgggag
1681  gctcgaccct taacgcctgg aaagggcaca gggagctgtg ttgtccgtca gtcgctgttg
1741  taactaagta gtgcatacac cgtggcttgt cacagtaatt ccgaagatg  tccaacgtta
1801  gttgagacaa ctgaacttct taccgtggca atcactcatt gtaacatcaa gttgaaaatg
1861  agggctgaag tttccctcac aggctaccat atgtgagata tgtccttcct ttgtaccact
1921  aagtggccct gtgtcatgta tgaatgtatc tcaatttgct attgcagaaa tgtttggtga
1981  aactttcaaa aaaaaaaaa  aaaaaaaaaa aa
```

SEQ ID NO. 2 memdgvlqaadakdwvykgegaanlilsytgsspsmlgkvlrlkkilknksqrapscivfssheqllwgh
ipelvesvkqgclaqayavhvmsqhlganhydggvrvrvsrdflelveknvlssrpagrvnassidntad
aalliadhslfsgnpkgssciaveikakcgflpsseyisedntikklvtrykmhqhlkfyqgeisktsey
npldlfsgskericmaikslfstpqnnlrifvngslafggmgggadsvhpaddkcledlskisglklpdf
tellsetifrsevlgnllatqklddhdiegvihlyyniisqpclvcknitdvellrkytflhslpldksl
kivrdflisatakdcslmisfrprengstdseydsvflesakrtyeykayfldldvkpldkmehyfkldq
rivnfytrngglaiskgq

SEQ ID NO. 3

```
   1  tcccttggta gacgaggcct tgacctgaac cgtgttcatc agtcttttgcg atttgtgctg
  61  agagtgctta ccagccgtgt ttatgagtgt tggaggtacc actaattacg gtacccgaca
 121  agaaatatca aataaaatag taattctggc atatatctag aagtgataaa taataaacaa
 181  tcaacttatg taacttggct aggtgcatcg caatgtccct atccctacc  agaaaaataa
 241  tcaaacacat catctacagt cctacaccat caccatcctc atcctcctcg agacgatcca
 301  catcctggaa cctattatgc catgcacgtt cccgacgatc accacataag tacatatttt
 361  ctatatttt  aattaaactt tttaaaataa tttcagaaaa aaacgataat tttgttttgt
 421  tttatgatgg agctaggaga gactgaattt cctcttgcaa ttttgggagt tttggacgga
 481  gcgagagcca gaattcgacg ctggcggcg  cgcgtcgcca atacgcagcg cggatgtgga
 541  gccacatgca aacgtgtgtc cgcccgcgtg gcgtccactc tccctccacg tttcggcgtc
 601  ctcgtcgcct tcctgggaaa tctccagcta ctgcccactg ccccttccct tcagtccctt
 661  tccccgggct gtggtaccag tactagtacc agcatctctt caggctccac caagcgcaga
 721  caccgcagca gcggcagcgg cacgatctgg tgaccccccg ccgcgtcaag cctgctcctc
 781  cggtgatcgc cggactggcg gggtaggaac cagcggagcg cagcccgcct ccttccgctg
 841  gtaagaccgt aagagtgacg cccgcccgct cctccctccg ctcgcttcct tgctctcccg
 901  attctggcgt accagtctca ccgcggcttg gggattggat acggagctag ttaaccagca
 961  gagctagata gcagatgcag attgcttgct tctctggttt gattttttgga gtcaccattt
1021  ctgtttggtt cgtgtgcctc ggtgtctgac agcagaagat cctcgatgga gatggatggg
1081  gttctgcaag ccgcggatgc caaggactgg gtttacaagg gggaaggcgc cgcgaatctc
1141  atcctcagct acaccggctc gtcgccctcc atggtaagcg ctgagtaggt tcttactgag
1201  cgtgcacgca tcgatcactt gactttaggg gctcaatgtg tgattcacgg gtgccgcggc
1261  gccattcgag ctccagatcc agtaccgctc gagcaagtga taaacatgg  agcagggacg
1321  atcacgtggt cacttgaaaa ttacgtgagg tccggggcga cgatgtacgg cgcggcgaac
1381  tctcaaacac tcacacaacc aaaaccgctt cgtgttcgtc tttgttccaa gcgactgtgt
1441  gagtgtttga gagttcgcca gcgcgacatc gcccgatctg acaaattaag ctttcgttgc
```

-continued

```
1501  ttttccatga ttgtgcattt tgtgagcatg cactgaatac tatgatggat atgtttggag 1561  gaagcattat tccaatttga tgataagggt gttatttaca cttgttttca gcttggcaag 1621  gtactgcggc tcaagaagat tctaaaaaac aagtcgcagc gggcaccgag ttgtattgta 1681  ttctcaagtc atgagcaact cctgtggggc catatcccag aactggttga gtcggtcaaa 1741  caagattgct tggctcaagc ctatgcagtg catgttatga gccaacacct gggtgccaat 1801  catgtcgatg gtggggtatg gttcagattc agttcattta tgtcctgtta ttgtgatttt 1861  gattggtaac atattgacaa cctcgacact tgggatcaga ttcagttcac ttatggaaga 1921  aattggagaa ttgttataat ttatctataa tcacccctac tgaaatagaa ataacatggc 1981  atcaatgtgc atgctattgg attttgacac gaatatgctt tattctatca tatgttggta 2041  attccagcag gcagcaggca ctactctttg gatccacgtg acttgacaaa gaaatcatgc 2101  catctttcca caatgcaggt ccgtgtacgt gtttctaggg attttctgga gcttgtcgaa 2161  aagaatgttc ttagcagccg tcctgctggg agagtaaatg caagttcaat tgataacact 2221  gctgatgccg ctcttctaat agcagaccac tctttatttt ctggtacgta ctctatccct 2281  cttcttacca taatctgaat cttgttaagg tttaaaatat atgattgatt aagtaaaatc 2341  cagagctcta ttcatatctc atgcactgat gttttgatga acacttgta gcaagacggt 2401  tgcctgttat ttctatttgc attagacgaa cagtcacctt tgtttataaa ggtctttgaa 2461  tttgcagttc ttataagttt aagtttgcaa ctgtcactta caacagccca atgggtagca 2521  tcaagattgt ttttttcagt gattcataac tcaactcttg gttaaaccgc tagaacattg 2581  ttggtgtctt aaaatgcaac tggtcctgag gccgtaacct gaaatcattg tactttctc 2641  tcatttcttt agatatttcc aaaactctac attagatgat ttatgtttgc ttacttagtc 2701  tttcttaatc tcaggcaatc ctaagggtag cagctgcata gctgtagaga taaaggtact 2761  ttgcaagctt cctctttat tcttatttt catttcttat gtatatttct cctcaaccat 2821  ttgacttctt ttcggcatgc tctaccttgc aggccaaatg tgggtttctg ccatcatcag 2881  aatatatatc agaagataat actatcaaga aactagtaac gagatataag atgcatcagc 2941  acctcaaatt ttatcagggt gaggtgtgta gattggaatg cttgatgcct tgatccaaga 3001  taaaattcca ctctcttttg cgcacttaaa aaacatccat cgatgataca aacttgatca 3061  aaataccta aggcttgtta tttacggcac tgttgtaata ttataccgtc tcttgctttt 3121  tgacatcagg ttgattccca atacattctt gcacacattt cagatatcga agactagtga 3181  gtacaatcct cttgatctat tttctgggtc aaaagagaga atatgcatgg ccatcaagtc 3241  ccttttctca actcctcaga acaacttaag gattttttgtc aatggatctt tagcttttgg 3301  tggcatggga ggtggtgcag atagtgttca tcctgctgac actcttaagt gtcttgaaga 3361  tctcagcaag attagtggcc taaaactccc tgacttcact gagctcctgt cagagacaat 3421  ttttaggtct gaggtattag caacctgtt ggccactcaa aagctggatg atcatgacat 3481  tgaaggggta attcatctgt actacaacat aatttctcag ccttgtttag tctgcaaaaa 3541  cctaactgat gtagagctat tgcggaagta cactttcttg cattctcttc cgttggacaa 3601  aagcctgaag atcgttaggg acttcctcat ttctgctacc gcaaaggact gtagcctgat 3661  gatcagcttt cggccaagag agaatggtag tacagattct gagtatgatt cagtgtttct 3721  tgaatcagcg aagcgaacct atgagtacaa ggtatactac tgtgaaatat ggtgtcgttt 3781  tacctttatc ttctaatcgt ccagcactct agccacaaaa ctagcaatat agttcacaag 3841  tgagtttgcc tgtggattta tttctttcct tattttcgg cataaatggt gctaagttga 3901  ccattcattt gcaggcatat ttccttgatc tggatgtgaa acctctggat aagatggagc
```

-continued

```
3961  attattttaa actggatcag aggatagtca atttctacac aagaaatggg ggaggtcttg
4021  ccatctccaa agggcagtaa taccaaagac acttcgagga ttcagctcca agaatgggga
4081  gcctctcttc ctgtatacat ctggagaagg gtgcatcagg gagtgttggt tgttgttcct
4141  gctgcttggt gctgctgttg taacttcatg agtacagtcc caaggttggg aggctcgacc
4201  cttaacgcct ggaaagggca cagggagctg tgttgtccgt cagtcgctgt tgtaactaag
4261  tagtgcatac accgtggctt gtcacagtaa tttccgaaga tgtccaacgt tagttgagac
4321  aactgaactt cttaccgtgg caatcactca ttgtaacatc aagttgaaaa tgagggctga
4381  agtttccctc acaggctacc atatgtgaga tatgtccttc ctttgtacca ctaagtggcc
4441  ctgtgtcatg tatgaatgta tctcaatttg ctattgcaga aatgtttggt gaaactttca
4501  tcctcccatg ctttgagcaa agctaaccta acttctttga atctgttggg cttattctag
4561  caaatcctgg ctgacggatg gacctgcgat gctgtctgct ttggctgtga tggctacagc
4621  ctgagcctac gggcacaagc gccagtcggc tgtcgccctc cagccactgt tcttgtctca
4681  tgattctgct atgtctgaag aactaggtaa ccggaaggca ccaagtgtga agtgtctcta
4741  gtactgcttg cttatatgtg tgttatttat ttgatcaaga actcacgtag cctttgattc
4801  ggcaacaccg tccggcgaaa gttggccgtt tgcagagcta gtcagggtgg ttcagcttcc
4861  agcctctaga cagagacaaa tgtgcttcgt gtttaaacag ttaggaattg cagctaagtg
4921  ggtgtttt t ttctatagac taattttagt ctcttcatta ttatatttta gtttctaaat
4981  taccaaatac gaaagctaaa actctatttt aatttctgta tctaataatt taagaactag
5041  aatggaataa aacagagaga ctaagaatta gtccctagaa accaaacaat ttctaaacta
5101  ttttttcaat aaagagtgtt tattaaactc aagatttagc atcacgccga tacaacacta
5161  aagagttcac gcccagcctc tgcacaacta tgcacaacta aggtgcacac aacctacaac
5221  tatgcacaac taaggtgcat acaacctggt aacacaaaac atgaaaaaca acaccaagcc
5281  aaatataact aaaataacga atggctgatc cgtagactag actgtcatcc atgtcaggga
5341  aaattgtccc tcgtcacacc cacacgctcc aactgtgtac acaactacac accttcaaaa
5401  acagctctct gccgaacgct gaagaggtcg cctactactg tgtatttcgt tagggtatca
5461  ggaccacgca cgtcaaagct gtggttttct gtcaccagcc gaaattcttg aacatcgcac
5521  aagaggtgaa acgatgctg caatgtagtc gctgagcaac gcaagttaga aagagaccga
5581  gagctggtgc tagcaattgt tattatgatg gccaatgcaa aggacagagt gaggcacgac
5641  ttttcttctc acccttacat tgtttataga atagaatcta aatacgagta tgaggatgga
5701  taaacggtag atagccttat aagttaatca ctcatcggct ttactctcga attggactat
5761  acttcagcag gaggagaact tgaaagaggt ggggtcggag ggacggttgc tcttggtgtg
5821  ggcagctacg aaccttttt ttttttttg gtcacatgga tagtacagcg gtctagtctt
5881  cggattaaag gctactgctg tgtttgtctt aaattttgct tatgttgctg gttgtgtgtt
5941  ctaaacagaa gctagaagaa cgtattgttt tttatatcta taaaatgctt ctttctttt
6001  atcgaaaaaa ggggacaaag cgaggcagcg agcgattgga cttctccatg caggggttga
6061  gctacccaat ttgtcgctcc aaccacctga aaactaacaa agaatatatg cggcagggga
6121  gctagcaaca cacctgccgg ccggcacttg ccactgtttc atgcaaggcc agagaaatta
6181  aagcggcggc gaagcaaagg gacccgggcg gccggcgtcc atgtcgaagg tgacggtgct
6241  caaggtggac acctcctgcg ccaaatgcaa gcgcaaggtc ctgcaggccg tcaccggcct
6301  ccatggtacg tacacggtat acacgtgcga gctagctatc ccgcttcttc ttcttctttg
```

-continued

```
6361 ttcggccatg catgcacagc acgcgcgcac catagattcc gttcccggca ataatgtaaa
6421 gatcgtttgg gctgggacgc tgggtgatgt gcggtgcgcg cgcaggtgtt gacaagatcg
6481 aggtggactc ggagaagagc acgatgacgg tgactggcac cgttggacccg gtggacgtga
6541 tcgtgcaggc gaggaaggcc gggaagcgcg cgtccgtgct caccatcggc cctccggcgc
6601 cgcccaagcc ggccgaggag aagaagcccg ctgagcagga taagaagaag gtggaggaga
6661 agaagacggc ggtggcgacg gcggcgggtg cggagaagaa ggcgcccgag acgccggcca
6721 cggtgttcgt ccaccacgtc ccgtcgtggc ctccgtgccc caggtaccag agagagtag
6781 tgtacgagca ggacccccg ccttgctcca tcatgtaatg taactatata cggatttgac
6841 caggagtata catgttcgtt tggaacgtag aacgcaagaa ctttgtaaga tcttgttctt
6901 ttgtattcta taaacttata gatgtgccag tgtcatggtc tgctggcacc gggacagaca
6961 cgcacgacgt gccacatggc atggatcgag ccaggcttca tgactgaccg actgttgaca
7021 tagctcatcg aatcactttt catgccaggt ttgtctaaaa aaataggccc tacgaaacct
7081 atgagactag cccgatcgag gcccgcgtgt taggaagaga gagagagtca ccgcgttcgt
7141 gctcgccgtc gtcaatggct caatgcacgg cgtgtactca acgcaatgga tcgatgaata
7201 aaatttgatg ttgatatatt agcacatcaa tccttttat attagacatg ttgtctttat
7261 tttttagaca aaaggtagta ccagtgacag tgacaaacac aaagacgaaa atttatggga
7321 ggacatgaag actgcatgac aaaattatga ccataaatgt ccatataatt caagttttat
7381 atcaatacac gatacaactt taaataaaga agttatatga ataaagaag caaacatacc
7441 gttaaatttt tgttgacaga gacaattgca tccttcttgt tttgagatgt cgaaatcacc
7501 gaataatgaa tttgaagatc tctttgagta taacaaacca ttaaaacgtt ccaattatct
7561 tcaatcttgt tacgcagttc tctcttaatt agctgaaaaa gttctcccaa cacttgccct
7621 tgacacatgt aataacatgg ccaactcaat tagcttgtag agtaaaggaa aggcaacata
7681 tgttttccgg ttgaaccgtc ttaatagaaa tagatgcaat atctttacaa acactaaaag
7741 cagcatgtct tctcacatga aagaatatat gtctcgagag ttactctctt aactctgcac
7801 gttcacacaa ctgtgaaatc ttgatcatat aactaactaa gattatctag attaagtaaa
7861 catataaaag gattttttgg atcaaagcaa gaaaaaccaa ctatcggctc acttgaagct
7921 tcactaaacc gatgacataa ctctgtattg attttatcaa aaataacaaa gaatatctcg
7981 atgtggtagt ggtaaagttg taaaggtttg tgactatgaa tccatctcgc ctctcataac
8041 ttctgcatct acgtggatta agatccataa tctaattttt ttgcaagcca ttaaattcac
8101 ctctcatatt cgatgaaccg tcatattcct attctccaat cttggatata gataagccct
8161 gatgatccag aataaaaaca ctagatatca aatccaaggt gtgtgtatag tagtatatct
8221 tgtcgaatgt caatcttgtt gaagggcgtc gaagcgtcgg gatggggca tgaatagggga
8281 aaaaattgct gcaatccggc tgcaaactag aatgtttata gaccctcaca aaaataagta
8341 tagacctcac ctgcaggtac atcagataac gttttagtta cgcgggctgc catgcatgaa
8401 cgcacgcgct aaaactttga aagacacagg cggctaatga tacttgactc tactgctagc
8461 tactgaaaac gtgcggtgag cacctttcgt ttctctcctt tatccctgtc ccgagcattg
8521 gtttgcggtt gtcctccaat tcaatttgat ctgggatctt gcgggaccat gcatgcctcc
8581 tccccatct tcttccccctt ctcgttcttc aacagggtct cttattactc tcttttgggc
8641 acgtgagatt tgagttttg aaagaccttg ttgttgtgtc acgagagttt tcgttatgat
8701 gatttttta gaactgttgt tgtttgatga aacttttacg tgtccacatc aatgcatgac
8761 ccgttgccta gatgctatcg ttgctaattt gctattctca actgcggcat ttctgcacat
```

```
8821 atgatttaaa actgtggctg cttgacatgt accgtagttt gctgaatcat gtgtctgcag 8881 caagcattta cacctgtcat ttgtacgtct gtggatcgtt gtggcggcca tggaacgcct 8941 tgagctcata taccagccgt gcccagtcac cggaagacga gccaccctcc gccacggcgg 9001 cgcgcgccgc ggccccgagc tcccgagatc tggctttcct cgccgctaac acctcctcgt 9061 cctgctggtc atcacccatg agcctcccca cggcgcgcac caccgcatca gccggcacca 9121 cagcctccaa gtccgactcg cgtacccgca cgcccacgcg gagcacctcc acgaggaaca 9181 gctcgttcag gaactgctcc gcgcggagcg gccacgtcgc gagcggcact ccggcggaca 9241 cggcctccag caccgagttc cagccgcagt gggtgacgaa gcctcccacc gcgcggtgcg 9301 ccaggatctc cgcctgtggc gccaccgcc cggccaccac catgccgttg ctggacgcgc 9361 gcgcctcccg ctccgcgcag ccgccgtccc cgccgggcgt cgtcgagacc acccagacga 9421 acggccggcc cgacgcgcgc agcccggtgg ccagctcacg aagctgggtc tcccccagcg 9481 agcacgtgct cccgaagcac acgtaaacca acgaaccctc gtccgggccg gcgagccact 9541 gcaaaatcgg gtcccgcttc gtaccgccgc tggcgacggg caaatgaaaa tggaaaaacc 9601 gtggggccca acaagaaaat tccttggcc tccccggaa ctggcctacg taatacccg 9661 ccaaattcgg cgtccaacgc a
```

---

What is claimed is:

1. A chimeric polynucleotide that encodes a plant inositol polyphosphate 2-kinase comprising a member selected from the group consisting of:
    (a) a polynucleotide comprising SEQ ID NO: 1;
    (b) a polynucleotide comprising at least 97% sequence identity to SEQ ID NO: 1, wherein the % sequence identity is based on the entire sequence of SEQ ID NO: 1 and is determined by GAP 10 analysis using default parameters and the Needleman and Wunsch algorithm; and,
    (c) a polynucleotide encoding a polypeptide comprising SEQ ID NO: 2.

2. The polynucleotide of claim 1, wherein the polynucleotide is DNA.

3. The polynucleotide of claim 1, wherein the polynucleotide is RNA.

4. The polynucleotide of claim 1, wherein the polynucleotide is a plant polynucleotide.

5. A chimeric polynucleotide that encodes an inositol polyphosphate 2-kinase having at least 98% sequence identity to SEQ ID NO: 1, wherein the % sequence identity is based on the entire sequence of SEQ ID NO: 1 and is determined by GAP 10 analysis using default parameters and the Needleman and Wunsch algorithm.

6. A chimeric polynucleotide that encodes SEQ ID NO:2.

7. The chimeric polynucleotide according to claim 6 encoding an inositol polyphosphate 2-kinase protein, wherein said polynucleotide hybridizes under stringent conditions with the full complement of SEQ ID NO: 1, and the stringent conditions include a wash step in 0.1×SSC at 60° C.

8. A chimeric polynucleotide that comprises a sequence of SEQ ID NO:1.

9. The polynucleotide of claim 1, wherein the polynucleotide comprises a sequence of a nucleic acid amplified from plant nucleic acid using primers based on SEQ ID NO: 1.

10. The polynucleotide of claim 1, wherein the inositol polyphosphate 2-kinase is a corn inositol polyphosphate 2-kinase.

* * * * *

SEQUENCE LISTING

<160> NUMBER OF SEQ ID NOS: 3

<210> SEQ ID NO 1
<211> LENGTH: 2012
<212> TYPE: DNA
<213> ORGANISM: Zea mays

<400> SEQUENCE: 1

```
cttcagtccc tttccccggg ctgtggtacc agtactagta ccagcatctc ttcaggctcc      60
accaagcgca gacaccgcag cagcggcagc ggcacgatct ggtgaccccc cgccgcgtca     120
agcctgctcc tccggtgatc gccggactgg cggggtagga accagcggag cgcagcccgc     180
ctccttccgc tgcagaagat cctcgatgga gatggatggg gttctgcaag ccgcggatgc     240
caaggactgg gtttacaagg gggaaggcgc cgcgaatctc atcctcagct acaccggctc     300
gtcgccctcc atgcttggca aggtactgcg gctcaagaag attctaaaaa acaagtcgca     360
gcgggcaccg agttgtattg tattctcaag tcatgagcaa ctcctgtggg gccatatccc     420
agaactggtt gagtcggtca aacaagattg cttggctcaa gcctatgcag tgcatgttat     480
gagccaacac ctgggtgcca atcatgtcga tggtggggtc cgtgtacgtg tttctaggga     540
ttttctggag cttgtcgaaa agaatgttct tagcagccgt cctgctggga gagtaaatgc     600
aagttcaatt gataacactg ctgatgccgc tcttctaata gcagaccact ctttattttc     660
tggcaatcct aagggtagca gctgcatagc tgtagagata aaggccaaat gtgggtttct     720
gccatcatca gaatatatat cagaagataa tactatcaag aaactagtaa cgagatataa     780
gatgcatcag cacctcaaat tttatcaggg tgagatatcg aagactagtg agtacaatcc     840
tcttgatcta ttttctgggt caaaagagag aaatatgcatg gccatcaagt cccttttctc     900
aactcctcag aacaacttaa ggattttgt caatggatct ttagcttttg gtggcatggg     960
aggtggtgca gatagtgttc atcctgctga cactcttaag tgtcttgaag atctcagcaa    1020
gattagtggc ctaaaactcc ctgacttcac tgagctcctg tcagagacaa ttttttaggtc    1080
```

-continued

```
tgaggtatta ggcaacctgt tggccactca aaagctggat gatcatgaca ttgaaggggt    1140
aattcatctg tactacaaca taatttctca gccttgttta gtctgcaaaa acctaactga    1200
tgtagagcta ttgcggaagt acactttctt gcattctctt ccgttggaca aaagcctgaa    1260
gatcgttagg gacttcctca tttctgctac cgcaaaggac tgtagcctga tgatcagctt    1320
tcggccaaga gagaatggta gtacagattc tgagtatgat tcagtgtttc ttgaatcagc    1380
gaagcgaacc tatgagtaca aggcatattt ccttgatctg gatgtgaaac ctctggataa    1440
gatggagcat tattttaaac tggatcagag gatagtcaat ttctacacaa gaaatggggg    1500
aggtcttgcc atctccaaag ggcagtaata ccaaagacac ttcgaggatt cagctccaag    1560
aacggggagc ctctcttcct gtatacatct ggagaagggt gcatcaggga gtgttggttg    1620
ttgttcctgc tgcttggtgc tgctgttgta acttcatgag tacagtccca aggttgggag    1680
gctcgaccct taacgcctgg aaagggcaca gggagctgtg ttgtccgtca gtcgctgttg    1740
taactaagta gtgcatacac cgtggcttgt cacagtaatt tccgaagatg tccaacgtta    1800
gttgagacaa ctgaacttct taccgtggca atcactcatt gtaacatcaa gttgaaaatg    1860
agggctgaag tttccctcac aggctaccat atgtgagata tgtccttcct ttgtaccact    1920
aagtggccct gtgtcatgta tgaatgtatc tcaatttgct attgcagaaa tgtttggtga    1980
aactttcaaa aaaaaaaaaa aaaaaaaaaa aa                                  2012
```

<210> SEQ ID NO 2
<211> LENGTH: 440
<212> TYPE: PRT
<213> ORGANISM: Zea mays

<400> SEQUENCE: 2

```
Met Glu Met Asp Gly Val Leu Gln Ala Ala Asp Ala Lys Asp Trp Val
1               5                   10                  15

Tyr Lys Gly Glu Gly Ala Ala Asn Leu Ile Leu Ser Tyr Thr Gly Ser
            20                  25                  30

Ser Pro Ser Met Leu Gly Lys Val Leu Arg Leu Lys Lys Ile Leu Lys
        35                  40                  45

Asn Lys Ser Gln Arg Ala Pro Ser Cys Ile Val Phe Ser Ser His Glu
    50                  55                  60

Gln Leu Leu Trp Gly His Ile Pro Glu Leu Val Glu Ser Val Lys Gln
65                  70                  75                  80

Gly Cys Leu Ala Gln Ala Tyr Ala Val His Val Met Ser Gln His Leu
                85                  90                  95

Gly Ala Asn His Val Asp Gly Val Arg Val Arg Val Ser Arg Asp
            100                 105                 110

Phe Leu Glu Leu Val Glu Lys Asn Val Leu Ser Ser Arg Pro Ala Gly
        115                 120                 125

Arg Val Asn Ala Ser Ser Ile Asp Asn Thr Ala Asp Ala Ala Leu Leu
    130                 135                 140

Ile Ala Asp His Ser Leu Phe Ser Gly Asn Pro Lys Gly Ser Ser Cys
145                 150                 155                 160

Ile Ala Val Glu Ile Lys Ala Lys Cys Gly Phe Leu Pro Ser Ser Glu
                165                 170                 175

Tyr Ile Ser Glu Asp Asn Thr Ile Lys Lys Leu Val Thr Arg Tyr Lys
            180                 185                 190

Met His Gln His Leu Lys Phe Tyr Gln Gly Glu Ile Ser Lys Thr Ser
        195                 200                 205
```

Glu Tyr Asn Pro Leu Asp Leu Phe Ser Gly Ser Lys Glu Arg Ile Cys
            210                 215                 220

Met Ala Ile Lys Ser Leu Phe Ser Thr Pro Gln Asn Asn Leu Arg Ile
225                 230                 235                 240

Phe Val Asn Gly Ser Leu Ala Phe Gly Gly Met Gly Gly Gly Ala Asp
                245                 250                 255

Ser Val His Pro Ala Asp Thr Leu Lys Cys Leu Glu Asp Leu Ser Lys
            260                 265                 270

Ile Ser Gly Leu Lys Leu Pro Asp Phe Thr Glu Leu Leu Ser Glu Thr
        275                 280                 285

Ile Phe Arg Ser Glu Val Leu Gly Asn Leu Leu Ala Thr Gln Lys Leu
    290                 295                 300

Asp Asp His Asp Ile Glu Gly Val Ile His Leu Tyr Tyr Asn Ile Ile
305                 310                 315                 320

Ser Gln Pro Cys Leu Val Cys Lys Asn Leu Thr Asp Val Glu Leu Leu
                325                 330                 335

Arg Lys Tyr Thr Phe Leu His Ser Leu Pro Leu Asp Lys Ser Leu Lys
            340                 345                 350

Ile Val Arg Asp Phe Leu Ile Ser Ala Thr Ala Lys Asp Cys Ser Leu
        355                 360                 365

Met Ile Ser Phe Arg Pro Arg Glu Asn Gly Ser Thr Asp Ser Glu Tyr
    370                 375                 380

Asp Ser Val Phe Leu Glu Ser Ala Lys Arg Thr Tyr Glu Tyr Lys Ala
385                 390                 395                 400

Tyr Phe Leu Asp Leu Asp Val Lys Pro Leu Asp Lys Met Glu His Tyr
                405                 410                 415

Phe Lys Leu Asp Gln Arg Ile Val Asn Phe Tyr Thr Arg Asn Gly Gly
            420                 425                 430

Gly Leu Ala Ile Ser Lys Gly Gln
        435                 440

<210> SEQ ID NO 3
<211> LENGTH: 9681
<212> TYPE: DNA
<213> ORGANISM: Zea mays

<400> SEQUENCE: 3
tcccttggta gacgaggcct tgacctgaac cgtgttcatc agtctttgcg atttgtgctg      60
agagtgctta ccagccgtgt ttatgagtgt tggaggtacc actaattacg gtacccgaca     120
agaaatatca aaataaatag taattctggc atatatctag aagtgataaa taataaacaa     180
tcaacttatg taacttggct aggtgcatcg caatgtccct atcccctacc agaaaaataa     240
tcaaacacat catctacagt cctacaccat caccatcctc atcctcctcg agacgatcca     300
catcctggaa cctattatgc catgcacgtt cccgacgatc accacataag tacatatttt     360
ctatattttt aattaaactt tttaaaataa tttcagaaaa aaacgataat tttgttttgt     420
tttatgatgg agctaggaga gactgaattt cctcttgcaa ttttgggagt tttggacgga     480
gcgagagcca gaattcgacg ctggcggcgg cgcgtcgcca atacgcagcg cggatgtgga     540
gccacatgca aacgtgtgtc cgcccgcgtg gcgtccactc tccctccacg tttcggcgtc     600
ctcgtcgcct tcctgggaaa tctccagcta ctgcccactg ccccttccct tcagtccctt     660
tccccgggct gtggtaccag tactagtacc agcatctctt caggctccac caagcgcaga     720
caccgcagca gcggcagcgg cacgatctgg tgaccccccg ccgcgtcaag cctgctcctc     780

```
cggtgatcgc cggactggcg gggtaggaac cagcggagcg cagcccgcct ccttccgctg      840
gtaagaccgt aagagtgacg cccgcccgct cctccctccg ctcgcttcct tgctctcccg      900
attctggcgt accagtctca ccgcggcttg gggattggat acggagctag ttaaccagca      960
gagctagata gcagatgcag attgcttgct tctctggttt gattttggga gtcaccattt     1020
ctgtttggtt cgtgtgcctc ggtgtctgac agcagaagat cctcgatgga gatggatggg     1080
gttctgcaag ccgcggatgc caaggactgg gtttacaagg gggaaggcgc cgcgaatctc     1140
atcctcagct acaccggctc gtcgccctcc atggtaagcg ctgagtaggt tcttactgag     1200
cgtgcacgca tcgatcactt gactttaggg gctcaatgtg tgattcacgg gtgccgcggc     1260
gccattcgag ctccagatcc agtaccgctc gagcaagtga taaaacatgg agcagggacg     1320
atcacgtggt cacttgaaaa ttacgtgagg tccggggcga cgatgtacgg cgcggcgaac     1380
tctcaaacac tcacacaacc aaaaccgctt cgtgttcgtc tttgttccaa gcgactgtgt     1440
gagtgtttga gagttcgcca gcgcgacatc gcccgatctg acaaattaag ctttcgttgc     1500
ttttccatga ttgtgcattt tgtgagcatg cactgaatac tatgatggat atgtttggag     1560
gaagcattat tccaatttga tgataagggt gttatttaca cttgttttca gcttggcaag     1620
gtactgcggc tcaagaagat tctaaaaaac aagtcgcagc gggcaccgag ttgtattgta     1680
ttctcaagtc atgagcaact cctgtggggc catatcccag aactggttga gtcggtcaaa     1740
caagattgct tggctcaagc ctatgcagtg catgttatga gccaacacct gggtgccaat     1800
catgtcgatg gtggggtatg gttcagattc agttcattta tgtcctgtta ttgtgatttt     1860
gattggtaac atattgacaa cctcgacact tgggatcaga ttcagttcac ttatggaaga     1920
aattggagaa ttgttataat ttatctataa tcacccctac tgaaatagaa ataacatggc     1980
atcaatgtgc atgctattgg attttgacac gaatatgctt tattctatca tatgttggta     2040
attccagcag gcagcaggca ctactctttg gatccacgtg acttgacaaa gaaatcatgc     2100
catctttcca caatgcaggt ccgtgtacgt gtttctaggg attttctgga gcttgtcgaa     2160
aagaatgttc ttagcagccg tcctgctggg agagtaaatg caagttcaat tgataacact     2220
gctgatgccg ctcttctaat agcagaccac tctttatttt ctggtacgta ctctatccct     2280
cttcttacca taatctgaat cttgttaagg tttaaaatat atgattgatt aagtaaaatc     2340
cagagctcta ttcatatctc atgcactgat gttttgatga acacttgta gcaagacggt      2400 tgcctgttat ttctatttgc attagacgaa cagtcacctt tgtttataaa ggtctttgaa     2460
tttgcagttc ttataagttt aagtttgcaa ctgtcactta caacagccca atgggtagca     2520
tcaagattgt ttttttcagt gattcataac tcaactcttg gttaaaccgc tagaacattg     2580
ttggtgtctt aaaatgcaac tggtcctgag gccgtaacct gaaatcattg tacttttctc     2640
tcatttcttt agatatttcc aaaactctac attagatgat ttatgtttgc ttacttagtc     2700
tttcttaatc tcaggcaatc ctaagggtag cagctgcata gctgtagaga taaaggtact     2760
ttgcaagctt cctctttat tcttatttt catttcttat gtatatttct cctcaaccat       2820
ttgacttctt ttcggcatgc tctaccttgc aggccaaatg tgggtttctg ccatcatcag     2880
aatatatatc agaagataat actatcaaga aactagtaac gagatataag atgcatcagc     2940
acctcaaatt ttatcagggt gaggtgtgta gattggaatg cttgatgcct tgatccaaga     3000
taaaattcca ctctcttttg cgcacttaaa aaacatccat cgatgataca aacttgatca     3060 aaataccta aggcttgtta tttacggcac tgttgtaata ttataccgtc tcttgctttt      3120
```

-continued

```
tgacatcagg ttgattccca atacattctt gcacacattt cagatatcga agactagtga      3180
gtacaatcct cttgatctat tttctgggtc aaaagagaga atatgcatgg ccatcaagtc      3240
ccttttctca actcctcaga acaacttaag gattttttgtc aatggatctt tagcttttgg    3300
tggcatggga ggtggtgcag atagtgttca tcctgctgac actcttaagt gtcttgaaga     3360
tctcagcaag attagtggcc taaaactccc tgacttcact gagctcctgt cagagacaat     3420
ttttaggtct gaggtattag gcaacctgtt ggccactcaa aagctggatg atcatgacat     3480
tgaaggggta attcatctgt actacaacat aatttctcag ccttgtttag tctgcaaaaa     3540
cctaactgat gtagagctat tgcggaagta cactttcttg cattctcttc cgttggacaa     3600
aagcctgaag atcgttaggg acttcctcat ttctgctacc gcaaaggact gtagcctgat     3660
gatcagcttt cggccaagag agaatggtag tacagattct gagtatgatt cagtgtttct     3720
tgaatcagcg aagcgaacct atgagtacaa ggtatactac tgtgaaatat ggtgtcgttt     3780 taccttatc ttctaatcgt ccagcactct agccacaaaa ctagcaatat agttcacaag      3840
tgagtttgcc tgtggattta tttctttcct tattttcgg cataaatggt gctaagttga      3900
ccattcattt gcaggcatat ttccttgatc tggatgtgaa acctctggat aagatggagc     3960 attatttaa actggatcag aggatagtca atttctacac aagaaatggg ggaggtcttg      4020
ccatctccaa agggcagtaa taccaaagac acttcgagga ttcagctcca agaatgggga    4080
gcctctcttc ctgtatacat ctggagaagg gtgcatcagg gagtgttggt tgttgttcct    4140
gctgcttggt gctgctgttg taacttcatg agtacagtcc caaggttggg aggctcgacc    4200
cttaacgcct ggaaagggca cagggagctg tgttgtccgt cagtcgctgt tgtaactaag    4260
tagtgcatac accgtggctt gtcacagtaa tttccgaaga tgtccaacgt tagttgagac    4320
aactgaactt cttaccgtgg caatcactca ttgtaacatc aagttgaaaa tgagggctga    4380
agtttccctc acaggctacc atatgtgaga tatgtccttc ctttgtacca ctaagtggcc    4440
ctgtgtcatg tatgaatgta tctcaatttg ctattgcaga aatgtttggt gaaacttttca   4500 tcctcccatg ctttgagcaa agctaaccta acttctttga atctgttggg cttattctag    4560
caaatcctgg ctgacggatg gacctgcgat gctgtctgct ttggctgtga tggctacagc    4620
ctgagcctac gggcacaagc gccagtcggc tgtcgccctc cagccactgt tcttgtctca    4680
tgattctgct atgtctgaag aactaggtaa ccggaaggca ccaagtgtga agtgtctcta    4740
gtactgcttg cttatatgtg tgttatttat ttgatcaaga actcacgtag cctttgattc    4800
ggcaacaccg tccggcgaaa gttggccgtt tgcagagcta gtcagggtgg ttcagcttcc    4860
agcctctaga cagagacaaa tgtgcttcgt gtttaaacag ttaggaattg cagctaagtg    4920
ggtgttttgt ttctatagac taattttagt ctccttcatta ttatatttta gtttctaaat   4980
taccaaatac gaaagctaaa actctatttt aatttctgta tctaataatt taagaactag    5040
aatggaataa aacagagaga ctaagaatta gtccctagaa accaaacaat ttctaaacta    5100 tttttttcaat aaagagtgtt tattaaactc aagatttagc atcacgccga tacaacacta   5160
aagagttcac gcccagcctc tgcacaacta tgcacaacta aggtgcacac aacctacaac    5220
tatgcacaac taaggtgcat acaacctggt aacacaaaac atgaaaaaca acaccaagcc    5280
aaatataact aaaataacga atggctgatc cgtagactag actgtcatcc atgtcaggga    5340
aaattgtccc tcgtcacacc cacacgctcc aactgtgtac acaactacac accttcaaaa    5400
acagctctct gccgaacgct gaagaggtcg cctactactg tgtatttcgt tagggtatca    5460
ggaccacgca cgtcaaagct gtggttttct gtcaccagcc gaaattcttg aacatcgcac    5520
```

```
aagaggtgaa acggatgctg caatgtagtc gctgagcaac gcaagttaga aagagaccga   5580
gagctggtgc tagcaattgt tattatgatg gccaatgcaa aggacagagt gaggcacgac   5640
ttttcttctc acccttacat tgtttataga atagaatcta aatacgagta tgaggatgga   5700
taaacggtag atagccttat aagttaatca ctcatcggct ttactctcga attggactat   5760
acttcagcag gaggagaact tgaaagaggt ggggtcggag ggacggttgc tcttggtgtg   5820
ggcagctacg aaccttttt tttttttttg gtcacatgga tagtacagcg gtctagtctt   5880
cggattaaag gctactgctg tgtttgtctt aaattttgct tatgttgctg gttgtgtgtt   5940
ctaaacagaa gctagaagaa cgtattgttt tttatatcta taaaatgctt cttttctttt   6000
atcgaaaaaa ggggacaaag cgaggcagcg agcgattgga cttctccatg caggggttga   6060
gctacccaat ttgtcgctcc aaccacctga aaactaacaa agaatatatg cggcagggga   6120
gctagcaaca cacctgccgg ccggcacttg ccactgtttc atgcaaggcc agagaaatta   6180
aagcggcggc gaagcaaagg gacccgggcg gccggcgtcc atgtcgaagg tgacggtgct   6240
caaggtggac acctcctgcg ccaaatgcaa gcgcaaggtc ctgcaggccg tcaccggcct   6300
ccatggtacg tacacggtat acacgtgcga gctagctatc ccgcttcttc ttcttctttg   6360
ttcggccatg catgcacagc acgcgcgcac catagattcc gttcccggca ataatgtaaa   6420
gatcgtttgg gctgggacgc tgggtgatgt gcggtgcgcg cgcaggtgtt gacaagatcg   6480
aggtggactc ggagaagagc acgatgacgg tgactggcac cgtggacccg gtggacgtga   6540
tcgtgcaggc gaggaaggcc gggaagcgcg cgtccgtgct caccatcggc cctccggcgc   6600
cgcccaagcc ggccgaggag aagaagcccg ctgagcagga taagaagaag gtggaggaga   6660
agaagacggc ggtggcgacg gcggcgggtg cggagaagaa ggcgcccgag acgccggcca   6720
cggtgttcgt ccaccacgtc ccgtcgtggc ctccgtgccc caggtaccag agagagtag   6780 tgtacgagca ggaccccccg ccttgctcca tcatgtaatg taactatata cggatttgac   6840
caggagtata catgttcgtt tggaacgtag aacgcaagaa ctttgtaaga tcttgttctt   6900
ttgtattcta taaacttata gatgtgccag tgtcatggtc tgctggcacc gggacagaca   6960
cgcacgacgt gccacatggc atggatcgag ccaggcttca tgactgaccg actgttgaca   7020
tagctcatcg aatcactttt catgccaggt ttgtctaaaa aaataggccc tacgaaacct   7080
atgagactag cccgatcgag gcccgcgtgt taggaagaga gagagagtca ccgcgttcgt   7140
gctcgccgtc gtcaatggct caatgcacgg cgtgtactca acgcaatgga tcgatgaata   7200
aaatttgatg ttgatatatt agcacatcaa tccttttat attagacatg ttgtctttat   7260 ttttagaca aaaggtagta ccagtgacag tgacaaacac aaagacgaaa atttatggga   7320
ggacatgaag actgcatgac aaaattatga ccataaatgt ccatataatt caagttttat   7380
atcaatacac gatacaactt taaataaaga agttatatga ataaaagaag caaacatacc   7440
gttaaatttt tgttgacaga gacaattgca tccttcttgt tttgagatgt cgaaatcacc   7500
gaataatgaa tttgaagatc tctttgagta taacaaacca ttaaaacgtt ccaattatct   7560
tcaatcttgt tacgcagttc tctcttaatt agctgaaaaa gttctcccaa cacttgccct   7620
tgacacatgt aatagcatgg ccaactcaat tagcttgtag agtaaaggaa aggcaacata   7680
tgttttccgg ttgaaccgtc ttaatagaaa tagatgcaat atctttacaa acactaaaag   7740
cagcatgtct tctcacatga aagaatatat gtctcgagag ttactctctt aactctgcac   7800
gttcacacaa ctgtgaaatc ttgatcatat aactaactaa gattatctag attaagtaaa   7860
```

```
catataaaag gatttttggg atcaaagcaa gaaaaaccaa ctatcggctc acttgaagct    7920
tcactaaacc gatgacataa ctctgtattg attttatcaa aaataacaaa gaatatctcg    7980
atgtggtagt ggtaaagttg taaaggtttg tgactatgaa tccatctcgc ctctcataac    8040
ttctgcatct acgtggatta agatccataa tctaattttt ttgcaagcca ttaaattcac    8100
ctctcatatt cgatgaaccg tcatattcct attctccaat cttggatata gataagccct    8160
gatgatccag aataaaaaca ctagatatca aatccaaggt gtgtgtatag tagtatatct    8220
tgtcgaatgt caatcttgtt gaagggcgtc gaagcgtcgg gatggggca tgaataggga     8280 aaaaattgct gcaatccggc tgcaaactag aatgtttata gaccctcaca aaaataagta    8340
tagacctcac ctgcaggtac atcagataac gttttagtta cgcgggctgc catgcatgaa    8400
cgcacgcgct aaaactttga aagacacagg cggctaatga tacttgactc tactgctagc    8460
tactgaaaac gtgcggtgag cacctttcgt ttctctcctt tatccctgtc ccgagcattg    8520
gtttgcggtt gtcctccaat tcaatttgat ctgggatctt gcgggaccat gcatgcctcc    8580
tcccccatct tcttcccctt ctcgttcttc aacagggtct cttattactc tcttttgggc    8640
acgtgagatt ttgagttttg aaagaccttg ttgttgtgtc acgagagttt tcgttatgat    8700
gattttttta gaactgttgt tgtttgatga aacttttacg tgtccacatc aatgcatgac    8760
ccgttgccta gatgctatcg ttgctaattt gctattctca actgcggcat ttctgcacat    8820
atgatttaaa actgtggctg cttgacatgt accgtagttt gctgaatcat gtgtctgcag    8880
caagcattta cacctgtcat ttgtacgtct gtggatcgtt gtggcggcca tggaacgcct    8940
tgagctcata taccagccgt gcccagtcac cggaagacga gccaccctcc gccacggcgg    9000
cgcgcgccgc ggccccgagc tcccgagatc tggctttcct cgccgctaac acctcctcgt    9060
cctgctggtc atcacccatg agcctcccca cggcgcgcac caccgcatca gccggcacca    9120
cagcctccaa gtccgactcg cgtacccgca cgcccacgcg gagcacctcc acgaggaaca    9180
gctcgttcag gaactgctcc gcgcggagcg gccacgtcgc gagcggcact ccggcggaca    9240
cggcctccag caccgagttc cagccgcagt gggtgacgaa gcctccacc gcgcggtgcg      9300 ccaggatctc cgcctgtggc gcccaccgcc cggccaccac catgccgttg ctggacgcgc    9360
gcgcctcccg ctccgcgcag ccgccgtccc cgcggggcgt cgtcgagacc acccagacga    9420
acggccggcc cgacgcgcgc agcccggtgg ccagctcacg aagctgggtc tcccccagcg    9480
agcacgtgct cccgaagcac acgtaaacca acgaaccctc gtccgggccg gcgagccact    9540
gcaaaatcgg gtcccgcttc gtaccgccgc tggcgacggg caaatgaaaa tggaaaaacc    9600
gtggggccca acaagaaaat ttccttggcc tcccccggaa ctggcctacg taatacccg     9660 ccaaattcgg cgtccaacgc a                                              9681
```